United States Patent
Noda et al.

(10) Patent No.: US 7,973,924 B2
(45) Date of Patent: Jul. 5, 2011

(54) TARGET SUBSTANCE SENSOR AND METHOD THEREOF USING A PHOTONIC CRYSTAL

(75) Inventors: Susumu Noda, Kyoto (JP); Takashi Asano, Kyoto (JP); Hitomichi Takano, Hirakata (JP)

(73) Assignees: Kyoto University, Kyoto-shi (JP); Panasonic Electric Works Co., Ltd., Kadoma-shi (JP)

( * ) Notice: Subject to any disclaimer, the term of this patent is extended or adjusted under 35 U.S.C. 154(b) by 645 days.

(21) Appl. No.: 10/593,646

(22) PCT Filed: Mar. 23, 2005

(86) PCT No.: PCT/JP2005/005249
§ 371 (c)(1),
(2), (4) Date: Jun. 26, 2008

(87) PCT Pub. No.: WO2005/090947
PCT Pub. Date: Sep. 29, 2005

(65) Prior Publication Data
US 2008/0252890 A1 Oct. 16, 2008

(30) Foreign Application Priority Data
Mar. 24, 2004 (JP) .................................. 2004-087666

(51) Int. Cl.
*G01J 3/00* (2006.01)
(52) U.S. Cl. ...................................................... 356/300
(58) Field of Classification Search .................. None
See application file for complete search history.

(56) References Cited

U.S. PATENT DOCUMENTS

| 5,872,359 | A | 2/1999 | Stewart et al. |
| 6,498,107 | B1 | 12/2002 | Fenner |
| 6,532,326 | B1 | 3/2003 | Hutchinson et al. |
| 7,433,035 | B2 * | 10/2008 | Gorelik et al. ............... 356/301 |
| 2002/0118937 | A1 | 8/2002 | Broderick et al. |

(Continued)

FOREIGN PATENT DOCUMENTS

CN 1195996 10/1998
(Continued)

OTHER PUBLICATIONS

Office Action dated Sep. 19, 2008, issued on the corresponding Chinese application and the English translation thereof.
(Continued)

*Primary Examiner* — Tu T Nguyen
(74) *Attorney, Agent, or Firm* — Edwards Angell Palmer & Dodge LLP

(57) ABSTRACT

A highly sensitive and compactable target substance sensor for detection of the target substance using a photonic crystal and a method thereof. The sensor includes an electromagnetic wave source of supplying an electromagnetic wave, a photonic sensor element, and a detector. The photonic sensor element has photonic crystalline structure and is configured to include a sensor waveguide for introducing the electromagnetic wave, and a sensing resonator electromagnetically coupled to the sensor waveguide for resonating the electromagnetic wave at specific wavelength. The sensing resonator is exposed to an atmosphere including the target substance so as to vary a characteristic of the electromagnetic wave emitted from the sensing resonator. The detector is configured to receive the electromagnetic wave emitted from the sensing resonator to recognize an intensity variation of the electromagnetic wave and issue a signal indicative of a characteristic of the target substance.

27 Claims, 13 Drawing Sheets

U.S. PATENT DOCUMENTS

| | | |
|---|---|---|
| 2002/0155592 A1 | 10/2002 | Kelleher et al. |
| 2002/0191884 A1 | 12/2002 | Letant et al. |
| 2003/0039446 A1 | 2/2003 | Hutchinson et al. |
| 2004/0023396 A1* | 2/2004 | Boyd et al. .................... 435/872 |
| 2004/0069948 A1 | 4/2004 | Feisst et al. |

FOREIGN PATENT DOCUMENTS

| | | |
|---|---|---|
| JP | 2003-262576 A | 9/2003 |
| JP | 2004-521476 | 7/2004 |
| JP | 2005-99007 | 4/2005 |
| WO | WO 02/50514 A1 | 6/2002 |
| WO | WO-2004/023114 A1 | 3/2004 |
| WO | WO 2005/022129 A1 | 3/2005 |

OTHER PUBLICATIONS

R.B. Wehrspohn, et al.; "Application of photonic crystals for gas detection and sensing;" ISBN: 3-527-40432-5; pp. 238-246./Discussed in the specification.

Office Action dated Aug. 4, 2009, issued on the Japanese application No. 2004-087666 and the English translation thereof.

Office Action dated Aug. 19, 2009, issued on the Canadian application No. 2,560,765.

M. Lončar et al., "Photonic crystal laser sources for chemical detection," Applied Physics Letters, vol. 82, No. 26, Jun. 30, 2003, pp. 4648-4650.

J. Topol'ančik et al., "Fluid detection with photonic crystal-based multichannel waveguides," vol. 82, No. 8, Feb. 24, 2003, pp. 1143-1145.

E. Chow et al., "Ultra compact biochemical sensor built with two-dimensional photonic crystal microcavity," Quantum Electronics Conference, 2004, (IQEC), May 2004, pp. 788-789.

Supplementary European Search Report dated Mar. 11, 2009, issued on the European patent application No. 05 72 7109.0.

* cited by examiner

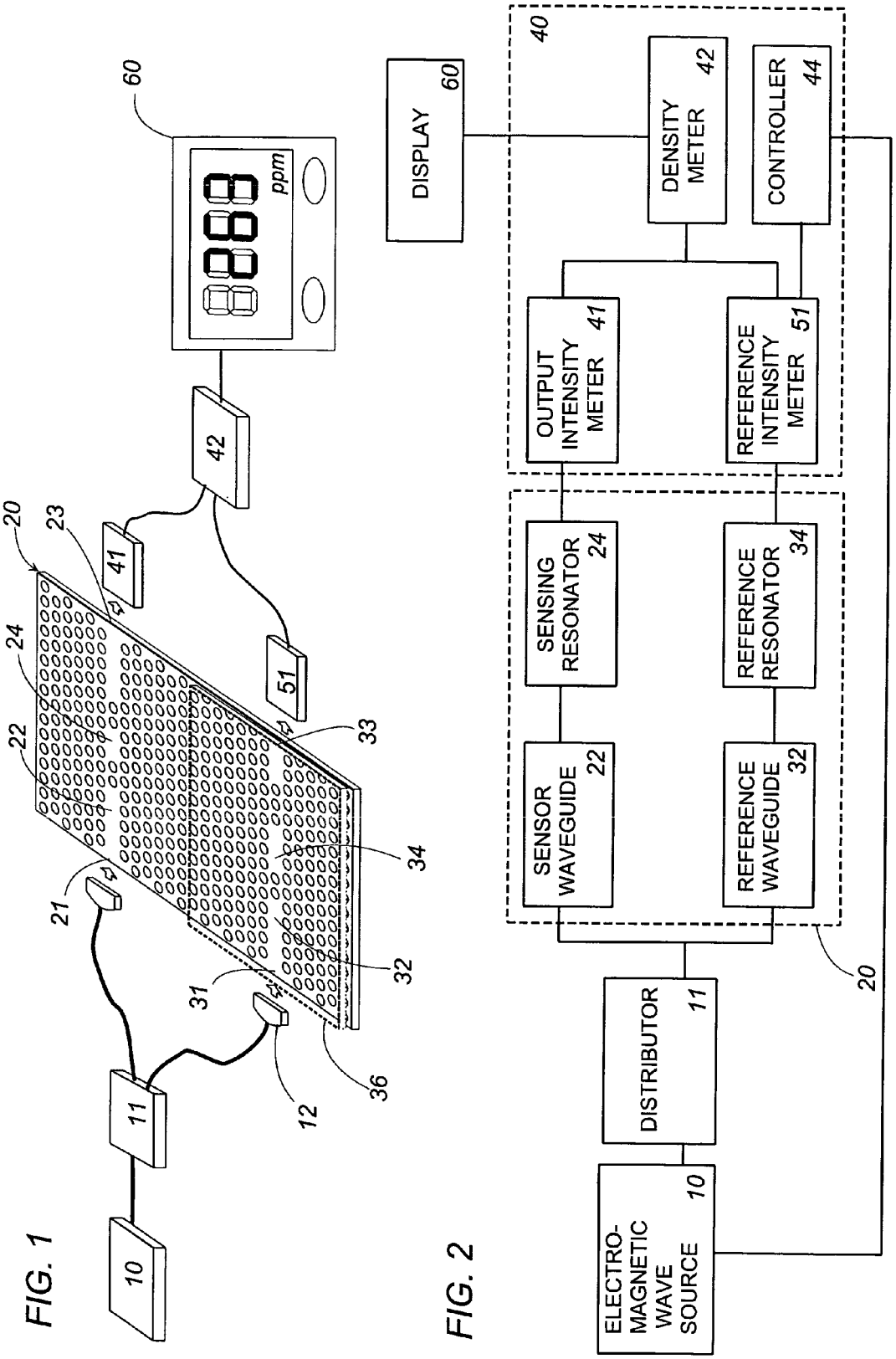

TARGET SUBSTANCE SENSOR AND METHOD THEREOF USING A PHOTONIC CRYSTAL

TECHNICAL FIELD

The present invention is directed to a sensor for detection of a target substance using a photonic crystal as well as a method thereof.

BACKGROUND ART

A prior art publication "Photonic Crystals" by R. Wehrspohn, ISBN3-527-40432-5, p. 238-246 discloses a sensor using a photonic crystal. The sensor uses a three-dimensional photonic crystal of bulk-type as a sensing element, and is configured to introduce a target gas through one of faces opposed with respect to the thickness of said sensing element, and to guide a light having a wavelength in match with an absorption wavelength of the target gas through the one face of the sensing element, thereby detecting the light emitted from the other face of the sensing element by use of a detector such as a photo-detector for calculating a gas density based upon the intensity of the detected light.

Generally, a group velocity Vg of the electromagnetic wave propagating within the photonic crystal is defined by $Vg=(d\beta/d\omega)^{-1}$, where $\beta$ is the propagation constant, and $\omega$ is a frequency. Therefore, the group velocity Vg becomes lower as a ratio of variation in the frequency $\omega$ to the variation of propagation constant $\beta$ becomes lower, and becomes zero when the relation between frequency $\omega$ and propagation constant $\beta$ satisfies a standing wave condition (end condition of waveguide mode).

The sensor disclosed in the publication is designed to elongate an optical path length by setting the group velocity Vg propagating in the three-dimensional photonic crystal to be about 30% of the light velocity in the vacuum, and is therefore required to give a thickness (i.e., a dimension along the direction of incident light) of several centimeters to the three-dimensional photonic crystal. In this consequence, the three-dimensional photonic crystal is required to have a uniform cyclic structure of refractive index in the order of 100 nm that satisfies the condition of the frequency $\omega$ and the propagation constant $\beta$ for obtaining the intended group velocity. However, when the cyclic structure of refractive index distorts, the group velocity goes out of the intended value at the distorted portion, which fails to make accurate density measurement. Therefore, the three-dimensional photonic crystal is required to be fabricated with an extremely precise manufacturing technology Further, since the three dimensional photonic crystal has a relatively large thickness, the propagation mode becomes multi-modes including the slower group velocity mode and higher group velocity mode, which may lower the sensitivity than with the constant group velocity. Also, since the sensitivity may vary when the coupling efficiency to various modes with respect to the incident light, the three dimensional photonic crystal is required to be positioned accurately in relation to the light source.

Further, since the electric field intensity distribution in space for the light of lower group velocity Vg is considerably different from the Gaussian distribution in space of the normal light, a complicated coupling structure for conversion of the electric field intensity distribution is required in order to avoid a light coupling loss which would be otherwise seen at the light incident face of the three dimensional photonic crystal to lower the sensitivity.

DISCLOSURE OF THE INVENTION

In view of the above problem, the present invention has been achieved to provide a target substance sensor which is highly sensitive to a target substance and compatible with the use of a photonic crystal and a method for detection of the target substance.

The sensor in accordance with the present invention includes an electromagnetic wave source of supplying an electromagnetic wave, a photonic sensor element, and a detector. The photonic sensor element has a photonic crystalline structure and configured to include a sensor waveguide for introducing the electromagnetic wave, and a sensing resonator electromagnetically coupled to the sensor waveguide in order to have the electromagnetic wave resonating at specific wavelength. The sensing resonator is exposed to an atmosphere including the target substance so as to vary a characteristic of the electromagnetic wave emitted from the sensing resonator. The detector is configured to receive the electromagnetic wave emitted from the sensing resonator to recognize an intensity variation of the electromagnetic wave and issue a signal indicative of a characteristic of the target substance. The sensor thus configured makes the use of resonance of the electromagnetic wave of the specific wavelength occurring at the resonator formed in the photonic crystal, for detecting the characteristic of the target substance based upon the intensity of the electromagnetic wave emitted from the resonator. In this consequence, the photonic sensor element can be made of a two-dimensional photonic crystal in which the sensor waveguide and the sensing resonator are arranged, and accordingly can be made into thin structure. In addition, the sensor can reduce the number of portions requiring precise photonic crystal structure than that required in the prior sensor relying upon the three-dimensional photonic crystal, and therefore can be manufactured at a lower cost.

Preferably, the detector is configured to determine a density of the target substance based upon a characteristic variation of said electromagnetic wave and issue said signal indicative of the density of the target substance.

For detection of the density of the target substance, different schemes are utilized depending upon the case of relying upon a phenomenon in which the target substance absorbs the electromagnetic wave of a specific wavelength and the case of relaying upon a phenomenon in which the electromagnetic wave emitted from the resonator has its wavelength shifted in the presence of the target substance.

When relying upon the phenomenon that the target substance absorbs the electromagnetic wave of the specific wavelength, the photonic sensor element is configured to additionally include a reference waveguide and a reference resonator within the photonic crystal structure. The reference waveguide is configured to introduce the electromagnetic wave from the electromagnetic wave source. The reference resonator is electromagnetically coupled to the reference waveguide to resonate the introduced electromagnetic waver at the specific wavelength. The detector is configured to include an output intensity meter providing a detection signal indicating an intensity of the electromagnetic wave of the specific wavelength emitted from the sensing resonator, a reference intensity meter providing a reference signal indicating an intensity of the electromagnetic wave of the specific wavelength emitted from said the resonator, and a density meter which compares the detection signal with the reference signal so as to obtain an attenuation of the electromagnetic wave of the specific wavelength, thereby calculating the density of the target substance based upon said attenuation. Accordingly, by designing the resonator to resonate the electromagnetic wave having the wavelength equal to that of the electromagnetic wave absorbed by the target substance, it is possible to make accurate density detection with reference to the electromagnetic wave absorption characteristic of the target substance.

In this instance, it is preferred that the photonic sensor element has the photonic crystalline structure arranged in a two-dimensional array, and each of the sensor waveguide and the reference waveguide extends within the two dimensional photonic crystalline structure to define an input port and an output port respectively on opposite ends of the waveguide. Each of the input ports is disposed to receive the electromagnetic wave from the electromagnetic wave source, while each of the output ports is coupled to each corresponding one of the output intensity meter and the reference intensity meter for providing the electromagnetic wave emitted from each corresponding one of the sensing resonator and the reference resonator.

Preferably, each of the aid sensing resonator and the reference resonator is disposed respectively within the sensor waveguide and the reference waveguide. Further, it is preferred that a plurality of the resonators are aligned in series within the corresponding waveguide to enhance a drop efficiency which is an output efficient of the emitted electromagnetic wave, thereby improving the detection sensitivity.

Further, the photonic sensor element may be configured to include a sensing output waveguide and a reference output waveguide. The sensing output waveguide and the reference output waveguide extend in parallel with corresponding ones of the sensor waveguide and the reference waveguide, and are electromagnetically coupled respectively to the sensor resonator and the reference resonator. Each of the sensing output waveguide and the reference output waveguide defines at its one lengthwise end an output port which is coupled to each corresponding one of the output intensity meter and the reference intensity meter.

Further, each of the output intensity meter and the reference intensity meter may be disposed in a spaced relation from a plane of the photonic sensor element, and coupled to each corresponding one of the sensing resonator and the reference resonator to receive the electromagnetic wave emitted therefrom.

Further, it is equally possible to make an input path of the electromagnetic wave common to the sensing resonator and the reference resonator. In this instance, the photonic sensor element is configured to include a first photonic crystalline structure and a second photonic crystalline structure which are of different configuration and arranged in side-by-side relation. The sensor waveguide includes an input waveguide extending across the first and second photonic crystalline structures, a first output waveguide extending within a confine of the first crystalline structure, and a second output waveguide extending within a confine of the second crystalline structure. The sensing resonator is formed within the first crystalline structure, while the second crystalline structure includes a reference resonator. The reference resonator is configured to cause a resonance of the electromagnetic wave of a wavelength ($\lambda 2$) different from the specific wavelength ($\lambda 1$) inherent to the sensing resonator. With this arrangement, by provision of the sensing resonator which resonates the electromagnetic wave of a first wavelength ($\lambda 1$) equal to that of the electromagnetic wave absorbed by the target substance, the electromagnetic wave of a second wavelength ($\lambda 2$) resonating at the reference resonator can be free from being influenced by the target substance, which eliminates a need of isolating the reference resonator from the atmosphere including the target substance.

In another preferred embodiment of the present invention, there is revealed a structure for density measurement of the target substance based upon the phenomenon that refractive index around a resonating portion will vary by contact with the target substance. When the refractive index varies around the resonating portion, the wavelength of the electromagnetic wave resonating at the resonating portion will shift. In this case, since the variation of the refractive index, i.e., the shifting amount of the resonating wavelength is determined inherent to the target substance, a density of the target substance can be obtained by detecting the intensity of the electromagnetic wave having the wavelength shifted in corresponding to the target substance. In order to realize this scheme, the electromagnetic wave source supplies the electromagnetic wave including different wavelengths to the sensing waveguide so that the sensing resonator allows the resonance of the electromagnetic wave of the specific wavelength determined by the target substance. In this connection, the detector is configured to select the electromagnetic wave of the specific wavelength (the electromagnetic wave of the wavelength varied due to the presence of the target substance) emitted from the sensing resonator, and is capable of calculating the density of the target substance through an analysis of the intensity of the selected electromagnetic wave of the specific wavelength. This scheme is effective for detection of the target substance which does not exhibit the absorption of the electromagnetic wave of the specific wavelength, and can eliminate the reference resonator and the associated elements for realizing more compact sensor.

Although a spectroscopic function is normally required to select the electromagnetic wave of the specific wavelength, it is possible to realize the scheme without the use of the spectroscopic function. For this purpose, the electromagnetic wave source is configured to generate the electromagnetic wave of variable wavelength and to supply to the photonic sensor element the electromagnetic wave of which wavelength varies with respect to time. A sweep range of the wavelength is set to include the specific wavelength determined by the refractive index of the target substance such that the detector obtains the electromagnetic wave intensity from the resonator when the electromagnetic wave of the specific wavelength is introduced, for density measurement of the target substance.

Further, the scheme of using the wavelength shift at the sensing resonator is available for detection of the target substances of various kinds. In this case, the sensor is configured to have a plurality of detection units each of which is composed of the sensing waveguide, the sensing resonator, and the detector. The sensing resonators of the individual detection units are so arranged to resonate the electromagnetic wave of the wavelength which are different from those at the resonators of the other detection unit, i.e., in accordance with the target substances, enabling to obtain the density of the various target substance based upon the corresponding electromagnetic wave intensity.

The sensing resonator is preferred to include, as a means for positively causing or enhancing the wavelength shift in response to the target substance, a reactor which reacts with the target substance to give significant change in the refractive index around the sensing resonator and therefore cause correspondingly significant wavelength shift.

When using the reactor, it is possible to apply the reactor to one of the two sensing resonators formed in the photonic sensor element. In this case, the density of the target substance reacting at the reactor can be determined by referencing a composite magnetic wave composed of the electromagnetic waves from the sensing resonator with the reactor and that without the reactor.

In the scheme of making the use of the wavelength shift of the electromagnetic wave resonating at the sensing resonator, a plurality of the sensing resonators are arranged in the two-dimensional array to make it easy to design a planar sensor. In this instance, a plurality of the detectors are arranged in a two-dimensional array in match with a plurality of the sensing resonators such that the individual detectors can determine different densities to give a density distribution of the target substance within the two-dimensional plane.

Further, it is equally possible to detect the kinds of the different target substances dispersed over a certain region, apart from the density of the target substance. In this instance, a plurality of sensing resonators are arranged in a two-dimensional array, while a plurality of detectors are arranged correspondingly in a two-dimensional array. The plural sensing resonators are configured to resonate the electromagnetic wave of different wavelengths such that the different kinds of the target substances can be identified based upon the intensities of the electromagnetic waves of specific wavelengths emitted respectively from the plural detectors, which enables to give a distribution of the different target substances within a two-dimensional plane.

Further, the present invention discloses an advantageous structure for determination of the density of the target substance based upon electromagnetic wave intensity variation caused by the provision of the reactor at a portion other than the sensing resonator. For example, when the reactor is disposed in the sensor waveguide, the refractive index of the sensor waveguide will vary by reaction with the target substance so as to vary an effective waveguide length between the sensor waveguide and the sensing resonator, which in turn varies intensity of the electromagnetic wave received at the detector. The detector is configured to calculate the density of the target substance based upon the variation of the intensity of the electromagnetic wave.

When the reactor is disposed in an energy coupling path between the two sensing resistors in the photonic sensor element, an effective waveguide length of the energy coupling path will vary by reaction with the target substance such the density of the target substance can be determined by analysis of the resulting electromagnetic wave intensity variation.

Further, the present invention proposes a structure of the photonic sensor element capable of highly sensitive density detection by the combination of the above-mentioned reactor with a particular photonic crystalline structure. The photonic sensor element includes a first photonic crystalline structure and a second photonic crystalline structure which are different from each other and are arranged in a side-by-side relation within a two-dimensional array. The sensor waveguide is composed of an input waveguide and an output waveguide which extend in parallel with each other. Each of the input and output waveguides extends over the full length of the first photonic crystalline structure into the second photonic crystalline structure. The sensing resonator is formed in the first crystalline structure between the input waveguide and the output waveguide to be electromagnetically coupled to the waveguides. The input waveguide defines at its one lengthwise end away from the second crystalline structure an input port for receiving the electromagnetic wave from the electromagnetic wave source. The output guide defines at its one lengthwise end away from the second crystalline structure an output port for emitting the electromagnetic wave of the specific wavelength resonating at the sensing resonator. The input waveguide is formed with an input reflector at the interface between the first and second crystalline structures for reflecting the electromagnetic wave of the specific wavelength towards said output port. Also, the output waveguide is formed with an output reflector at the interface between the first and second crystalline structures for reflecting the electromagnetic wave of the specific wavelength towards the input port. Each of thus configured input waveguide and output waveguide is provided with a reactor at a portion bridging across the first and second crystalline structures. The reactor is configured to react with the target substance to alter reflection efficiency, thereby varying the intensity of the electromagnetic wave received at the target detector. The detector is arranged to calculate the density of the target substance as a function of the intensity. Since the input waveguide and the output waveguide are arranged to bridge over the different photonic crystalline structures with the reflectors disposed therebetween, and also since the input waveguide and the output wave guide are formed at the respective portions bridging over the different photonic crystalline structures with the reactors which vary the characteristic of the electromagnetic wave in response to the presence of the target substance, the reflectors can amplify the refractive index variation to give a phase shift of the electromagnetic wave propagating towards the sensing resonator, thereby enhancing a drop efficiency of the electromagnetic wave of the specific wavelength resonating at the sensing resonator and being emitted therefrom for assuring highly sensitive density detection of the target substance.

The sensor of the present invention is preferred to include a controller which is configured to monitor an environmental parameter indicative of an environmental condition. The controller is provided to modify an optical characteristic of the sensing resonator based upon the environmental parameter to resonate the electromagnetic wave at the specific wavelength for enabling the accurate measurement in compensation for external disturbances such as temperature. For example, the photonic sensor element may be provided with a heater which is actuated by the controller to manage the temperature of the sensing resonator in order to modify the optical characteristic of the photonic sensor element for keeping the characteristic of the sensing resonator at a constant.

Also, the sensor of the present invention is preferred to include a refresh means which is configured to eliminate the target substance or impurities trapped on the sensing resonator. The refresh means may be a heater which dissipates the target substance or impurities from the surface of the sensing resonator by heat.

Further, the heater may be used as a modulating means which modulates one of the wavelength and the intensity of the electromagnetic wave propagating in the waveguide. That is, the periodical energization of the heater can modulate the intensity or the wavelength of the electromagnetic wave emitted from the resonator on a periodical basis. Thus, only the modulated electromagnetic wave can be selected at the detector so as to be discriminated from noise electromagnetic waves for improving the detection accuracy.

The present invention further provides a method of detecting the density of the target substance by use of the photonic crystal. This method utilizes a photonic sensor element which is configured to include a sensor waveguide introducing an electromagnetic wave, and a sensing resonator electromagnetically coupled to the waveguide for resonating the electromagnetic wave of the specific wavelength. The method includes the steps of exposing the sensing resonator to an atmosphere including the target substance, and introducing the electromagnetic wave including the specific wavelength through the sensor waveguide, detecting an intensity of the electromagnetic wave resonating at the sensing resonator; and analyzing the intensity to calculate a density of said target substance.

BRIEF DESCRIPTION OF THE DRAWINGS

FIG. 1 is a schematic view illustrating a sensor in accordance with a first embodiment of the present invention;
FIG. 2 is a functional block diagram of the above.

BEST MODE FOR CARRYING OUT THE INVENTION

Figure 3:
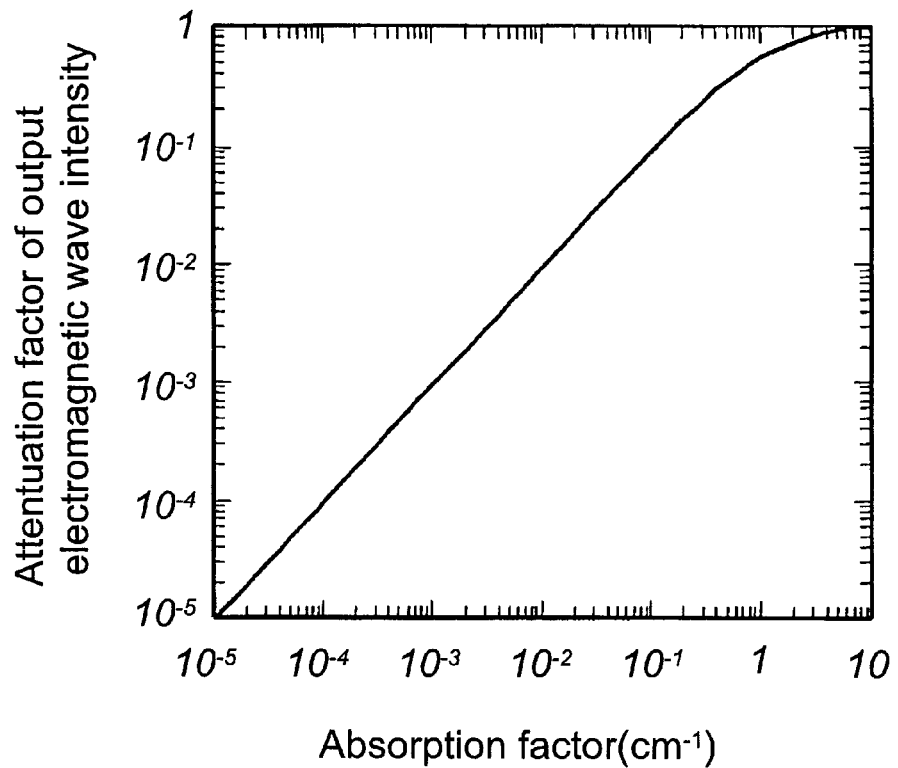
FIG. 3 is a graph illustrating the density detection of the above.

The sensor in accordance with the present invention employs a photonic sensor element 20 having a two-dimensional photonic crystalline structure. The photonic crystalline structure a matrix and a material which is arranged in the matrix and has a refractive index different from that of the matrix to be give an optical characteristic of alternating a direction and a propagation velocity of an incident magnetic wave. The present invention uses the photonic crystal having the matrix of a silicon semiconductor (250 nanometers thickness) with a refractive index of 3.4, and minute circular pores (φ=240 nanometers) arranged in two-dimensional array within the matrix at a pitch of 420 nanometers. Thus, the air with a refractive index of 1 present in the minute pores is cyclically dispersed within the substrate (refractive index of 3.4) to give the photonic crystal characteristic. The silicon semiconductor is carried on an oxidized silicon layer, i.e., SOI substrate (refractive index of 1.5). That is, the photonic crystal is made of the SOI substrate of which silicon semiconductor layer is etched to develop a large number of circular pores to realize the photonic crystalline structure within the silicon semiconductor layer.

The photonic sensor element 20 is formed with a waveguide 22 for introducing the electromagnetic wave and a resonator 24 which resonates one of the electromagnetic waves introduced into the waveguide having a specific wavelength. The waveguide and the resonator is formed by providing defects, i.e., the portions without the pores, to the cyclic structure in the photonic crystalline structure.

When using the electromagnetic wave within an optical transmission bandwidth such as a C-band (1530 nm to 1565 nm) or L-band (1565 nm to 1625 nm), the circular ports in the photonic crystalline 1 is arranged in an array at a cycle (a) of 0.42 μm (i.e., the cycle of the refractive index cyclic structure the two-dimensional photonic crystal, or an inter-lattice distance between lattice points of two-dimensional triangular lattice), the circular pores is given a radius of 0.92 a, and the sensor element is given a thickness of 0.6 a. Thus, there is formed a photonic band gap of a bandwidth which does not propagate the electromagnetic wave (light) of the above frequency bands incident in any direction in the two-dimension perpendicular to the thickness of the photonic crystal. The waveguide 22 and the resonator 24 are devoid of suitable number of the circular pores for enabling to propagate the electromagnetic wave. The values for the cycle (a) and the radius of the circular pore are not limited to the above, and the cycle (a) may be nearly the wavelength of the electromagnetic wave of the above bandwidths (for example, half of the wavelength of the electromagnetic wave).

The present invention is configured to detect a density of a target substance by making the use of the resonance occurring at the resonator within the photonic crystal, and makes the density detection through different mechanism according to the kinds of the target substances. The target substances can be basically classified into the following two classes.
1) Those exhibiting a prominent character of absorbing an electromagnetic wave of a specific wavelength; and
2) Those exhibiting a prominent character of altering the refractive index of an atmosphere.

The present invention relies upon the above two characters depending upon the kinds of the target substances, and is first explained with reference to a first embodiment for the density detection by making the use of the above 1) character.

1st Embodiment

In the present embodiment, the electromagnetic wave of the specific wavelength that the target substance absorbs is caused to resonate at the resonator so as to detect the target substance based upon an attenuation factor of the output from the resonator. The applicable target substance includes that has a prominent character of absorbing the electromagnetic wave of the specific wavelength, for example, carbonic acid gas and nitrogen gas, and the like gas.

FIGS. 1 and 2 illustrates the sensor in accordance with the present embodiment in which the photonic sensor element 20 is formed with a senor waveguide 22 and a reference waveguide 32 which introduce the electromagnetic waves including that having the specific wavelength, for example, an infrared ray having a wavelength of 2 μm to 13 μm, as well as a sensing resonator 24 and a reference resonator 34 which are electromagnetically coupled respectively to the waveguides. The resonators are each configured to resonate the electromagnetic wave of the specific wavelength (absorbed in the target substance). The sensing resonator 24 and the sensor waveguide 22 are exposed to an atmosphere containing the target substance to measure the intensity of the electromagnetic wave absorbed by the presence of the target substance. While on the other hand, the reference waveguide 32 and the reference resonator 34 are isolated by means of a shield 36 from the atmosphere containing the target substance to obtain a reference intensity of the electromagnetic wave such that the attenuation factor of the electromagnetic wave is obtained from the difference of the two intensities for determination of the density of the target substance based upon the attenuation factor.

In order to achieve the above function, the sensor in accordance with the present embodiment is provided with an electromagnetic wave source 10 for supplying the electromagnetic wave to the photonic sensor element 20, a distributor 11 for distributing the electromagnetic wave to the sensor waveguide 22 and the reference waveguide 32, an output intensity meter 41 for measuring the intensity of the electromagnetic wave emitted from the sensing resonator 24, a reference intensity meter 51 for measuring the intensity of the electromagnetic wave emitted from the reference resonator 34, an a density meter 42 which obtains the attenuation factor of the electromagnetic wave from the difference of the intensities of the electromagnetic waves obtained at the both meters for determining the density of the target substance. The output intensity meter 41, the reference intensity meter 51, and the density meter 42 are collectively referred to as a detector 40, and is realized in a single microprocessor. The detector 40 outputs a density signal indicative of the density obtained at the density meter 42 to a display 60 for display of the density.

The sensor waveguide 22 and the reference waveguide 32 extend linearly over the full-length of the photonic sensor element to define input ports 21 and 31 at one longitudinal ends, and output ports 23 and 33 at the other longitudinal ends. Feeders 12 are coupled respectively to the input ports 21 and 31 to introduce the electromagnetic wave from the source to the individual waveguides. The output ports 23 and 33 are respectively coupled to the output intensity meter 41 and the reference intensity meter 51 to transmit the electromagnetic wave of the specific wavelength emitted from the sensing resonator 24 and the reference resonator 34 to the intensity meters. The sensing resonator 24 and the reference resonator 34 are each formed in the longitudinal center of each corresponding waveguide to propagate the electromagnetic wave resonating at the corresponding resonator. The intensity meter 41 provides a detection signal indicating the intensity of the electromagnetic wave resonating at the resonator 24, while the intensity meter 51 provides a reference signal indicating the intensity of the electromagnetic wave resonating at the resonator 34. The density meter 42 determines the attenuation factor occurring due to the presence of the target substance from the difference of the detection signal of the output intensity meter 41 and the reference signal of the reference intensity meter. The attenuation factor is expressed by the following equation 1.

$$L = \frac{Iref - Iout}{Iref} \quad \text{(equation 1)}$$

wherein Iref is the output from the reference intensity meter 51, and Iout is the output from the output intensity meter 41. Thus obtained attenuation factor (L) is found to have a relation with absorption factor of the target substance as shown in FIG. 3. Since the absorption factor corresponds to the density of the target substance in the atmosphere, and the detector 40 is configured to have an equation indicating the relation between the attenuation factor and the density, the density meter 42 can determined the density of the target substance based upon the attenuation factor. The output intensity of the electromagnetic wave is determined by the following equation 2.

$$Iout = \frac{1}{\left(1 + \frac{Qin}{2Qa}\right)} \quad \text{(equation 2)}$$

Qin is a Q-value determined by a coupling intensity between the resonator and the waveguide, while Qa is a Q-value determined by an amount of energy loss absorbed within the resonator. In more details, Qin is Q-value between the resonator and the waveguide, Qa is Q-value resulting from the absorption at the resonator, and Qy is determined by Q-value between the resonator and a free space and satisfies a relation of Qy>>Qin. Qin is regarded as a value relating to an amount of energy leaking from the resonator to the waveguide in a system of the resonator and the waveguide (namely, a value indicating an amount of energy being accumulated in the resonator in the system of the resonator and the waveguide). When expressing the energy accumulated in the resonator as W, and the energy loss in a unit time from the resonator to the waveguide as dW/dt, it is defined that $Qin=\omega_0 \times W/(dW/dt)$ is defined. Qa is regarded as a value relating to an amount of energy lost by the absorption in the resonator. When expressing the energy accumulated in the resonator as W, and the energy loss in a unit time by the absorption in the resonator as −dW/dt, it is defined that $Qa=\omega_0 \times W/(dW/dt)$, and therefore $Qa=(\omega_0 \times n_m)/(\alpha \times c)$ wherein nm is an effective refractive index of the resonator 24, α is the absorption factor, and c is the light velocity.

In this connection, the output intensity of the electromagnetic wave is known as drop efficiency (D) which is expressed by a ratio of the electromagnetic wave intensity $S_{+1}$ introduced to the input port to the electromagnetic wave intensity $S_{-2}$ emitted from the output port, as shown in the below equation.

$$D = \left|\frac{S_{-2}}{S_{+1}}\right|^2 \quad \text{(equation 3)}$$

The scheme as indicated in FIG. 2 includes a controller 70 which monitors an intensity of the electromagnetic wave output from the electromagnetic wave source 10 to maintain the output intensity at a constant by a feedback control in order to compensate for external disturbances to make a stable measurement.

In addition to the configuration of FIG. 1, the photonic sensor element may be configured as shown in FIGS. 4 to 9. Although the structures are explained only with regard to the sensor waveguide 22 and the sensing resonator 24, the like configuration can be applied to the reference waveguide and the reference resonator.

Figure 4:
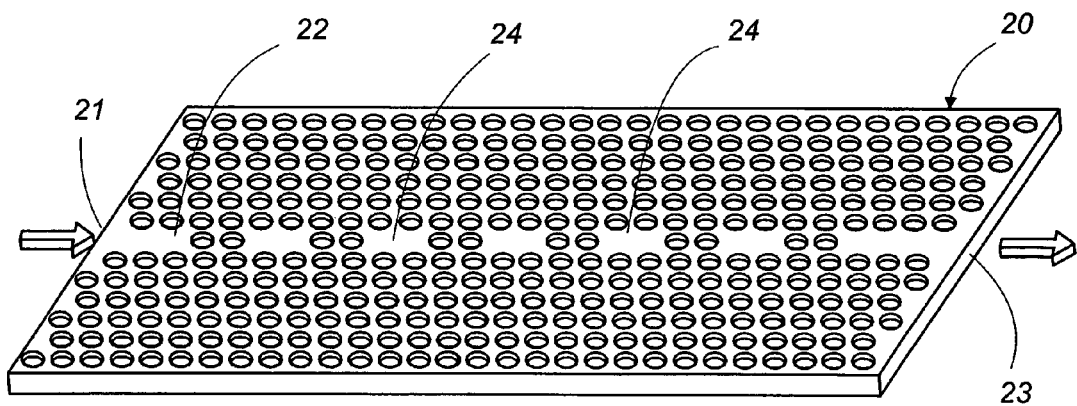
FIG. 4 is a perspective view of another example of the photonic sensor element employed in the above.

The photonic sensor element 20 of FIG. 4 is formed with a plurality of the sensing resonators 24 within the sensor waveguide 22, and is formed at opposite lengthwise end respectively with the input port 21 and the output port 23 of the electromagnetic wave. Each sensing resonator 24 is designed to resonate the same electromagnetic wave of the specific wavelength, and is provided to increase a chance of contacting with the target substance for improving the detection sensitivity of the target substance.

Figure 5:
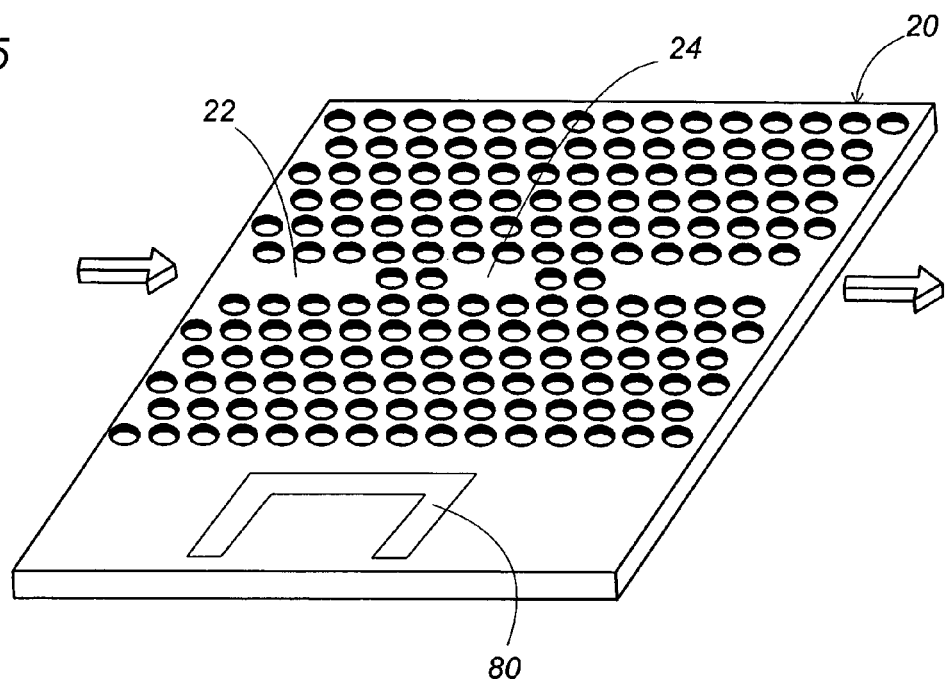
FIG. 5 is a perspective view of a further of the photonic sensor element employed in the above.

The photonic sensor element 20 of FIG. 5 is formed integrally with a heater 80 by which a thermal control is made to maintain a uniform optical characteristic of the photonic sensor element for precise density detection of the target substance. The thermal control is made by use of a temperature sensor and is made by a controller shown in FIG. 2. In addition to this purpose, the heater 80 can be utilized to dissipate the target substance and impurities from the sensing resonator by heat. The heating of the heater at suitable timing can refresh the sensor element. The heater is preferably made of the Peltier element.

Further, the heater can be utilized as modulating means for modulating the wavelength or intensity of the electromagnetic wave propagating in the waveguide. That is, periodical energization of the heater can periodically modulate the intensity or the wavelength of the electromagnetic wave emitted from the resonator such that an analyzer can select only the modulated electromagnetic wave from those detected at the detector so as to discriminate it from electromagnetic wave noises arriving from other than the resonator for improving the detection accuracy. The modulating means is not limited to the heater, and may include those capable of wavelength modulation or intensity modulation of the electromagnetic wave from the electromagnetic wave source. For instance, the modulating means may be configured to include a chopping rotary plate and a motor which is controlled by the controller to drive the chopping rotary plate in order to periodically interrupt the output from the electromagnetic wave source.

Figure 6:
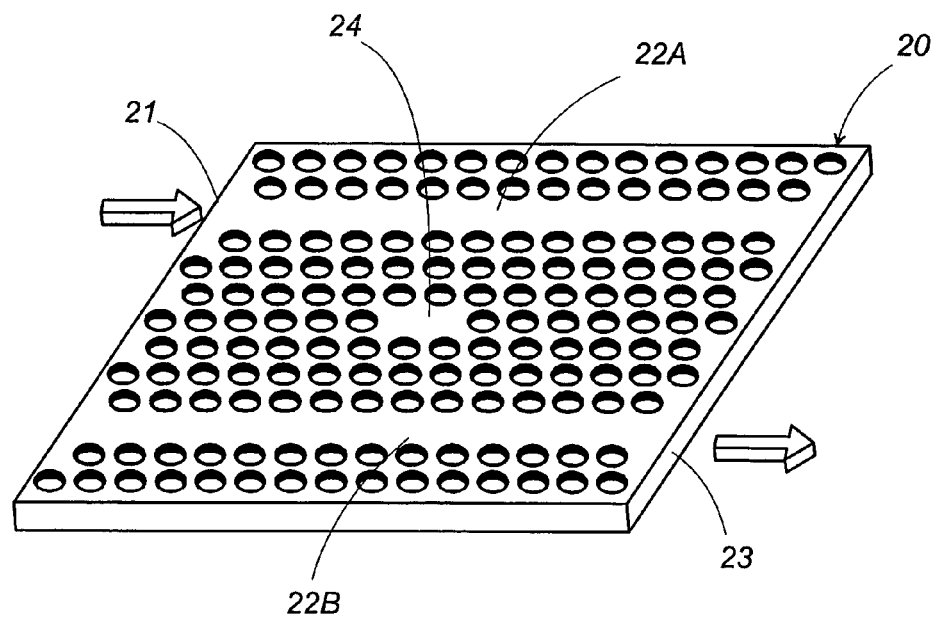
FIG. 6 is a perspective view of a further example of the photonic sensor element employed in the above.

In the photonic sensor element 20 of FIG. 6, the sensor waveguide is composed of an input waveguide 22A and an output waveguide 22B which extend in parallel with each other. The sensing resonator 24 is disposed at an intermediate portion between the input waveguide 22A and the output waveguide 22B to receive the electromagnetic wave of the specific wavelength from the input port 21 at one end of the input waveguide 22A and to resonate the electromagnetic wave thereat. The electromagnetic wave propagates through the output waveguide 22B so as to be emitted to the detector through an output port 23 at one of the waveguide.

Figure 7:
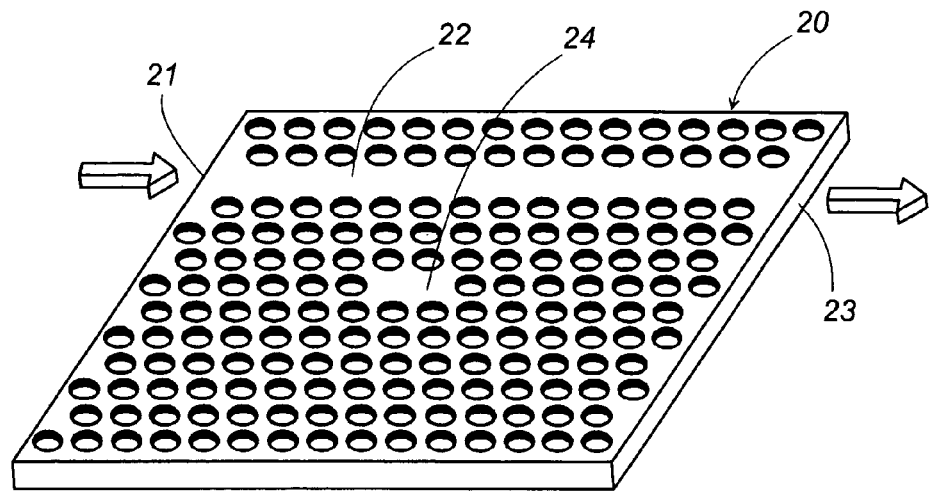
FIG. 7 is a perspective view of a further example of the photonic sensor element employed in the above.

In the photonic sensor element 20 of FIG. 7, the sensor waveguide 22 defines the input port 21 and the output port 23 respectively at its opposite lengthwise ends, while the sensing resonator 24 is formed at a portion spaced in a width wise direction of the photonic sensor element 20, i.e., spaced in a direction perpendicular to the lengthwise direction of the sensor waveguide so that the electromagnetic wave emitted from the sensing resonator 24 is output to the detector though the output port 23.

Figure 8:
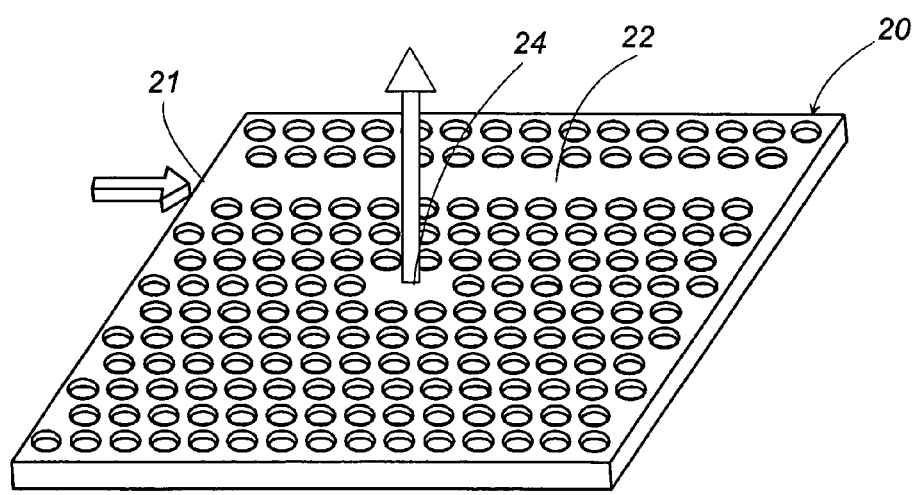
FIG. 8 is a perspective view of a still further example of the photonic sensor element employed in the above.

The photonic sensor element 20 of FIG. 8 is configured to emit the electromagnetic wave from the sensing resonator 24 in a thickness direction of the photonic sensor element for electromagnetically coupling the sensing resonator 24 to the detector disposed upwardly of the sensing resonator.

In the above embodiment, the sensor waveguide 22 and the sensing resonator 24 are cooperative with the detector 40 to give a single detection unit which detects the density of the target substance of one kind. Accordingly, it is possible to measure the densities of the target substance of different kinds by providing more than one detection units in association with different kinds of the target substances. In this instance, more than one sensing resonators resonating the electromagnetic wave of different wavelengths are formed together with the corresponding number of the sensor waveguides in one photonic sensor element.

2nd Embodiment

Figure 9:
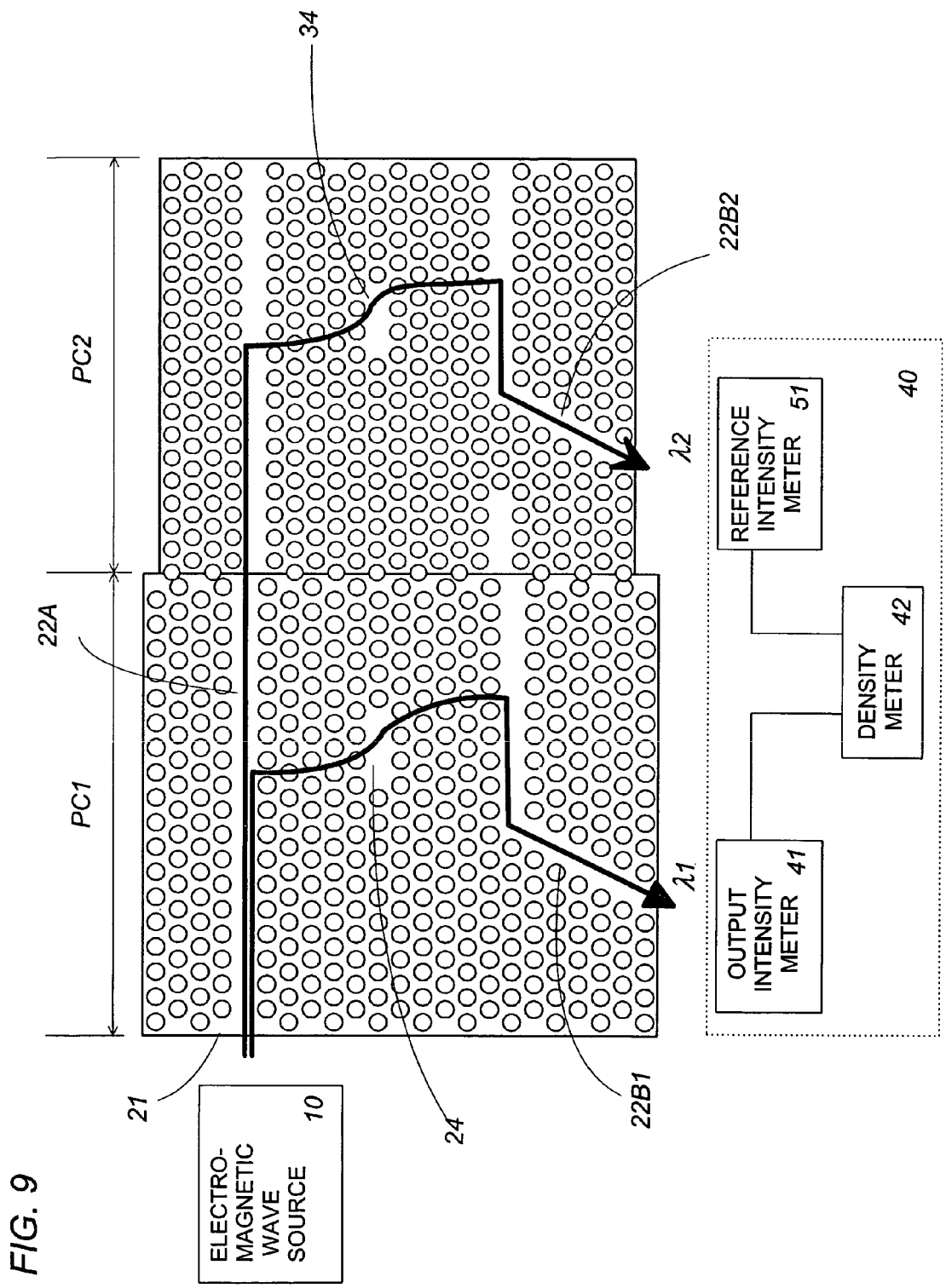
FIG. 9 is a schematic view illustrating a sensor in accordance with a second embodiment of the present invention.

FIG. 9 illustrates a second embodiment of the present invention in which the photonic sensor element 20 is configured to supply the electromagnetic wave from the source 10 to the sensing resonator 24 and the reference resonator 34 through a single input port 21. The photonic sensor element 20 is formed with a first photonic crystalline structure PC1 and a second photonic crystalline structure PC2 which are of different crystalline structures from each other. That is, the two different crystalline structures have minute circular pores of altering the refractive index which are arranged at different cycles within the two-dimensional array to selectively propagate the electromagnetic wave of different wavelengths. The sensor waveguide includes an input waveguide 22A extending over the two crystalline structures PC1 and PC2, and two output waveguides 22B1 and 22B2 belonging to each of the crystalline structures. The sensing resonator 24 and the reference resonator 34 are respectively formed in the crystalline structures PC1 and PC2 to be electromagnetically coupled to the input waveguide 22A and the output waveguides 22B1 and 22B2. The photonic crystalline structures PC1 and PC2 are designed to resonate the electromagnetic waves of wavelength different from each other at the resonators 24 and 34. That is, the first photonic crystalline structure PC1 causes the resonance for the electromagnetic wave having the first wavelength ($\lambda 1$) which is absorbed by the target substance, while the second photonic crystalline structure PC2 causes the resonance for the electromagnetic wave having the second wavelength ($\lambda 2$) other than the wavelength ($\lambda 1$). The detector 40 having the same configuration as shown in FIGS. 1 and 2 is employed such that the output intensity meter 41 detects the intensity of the electromagnetic wave having the first wavelength ($\lambda 1$), while the reference intensity meter 51 detects the intensity of the electromagnetic wave having the second wavelength ($\lambda 2$). The density meter 42 compares the electromagnetic wave intensity of the first wavelength ($\lambda 1$) and that of the second wavelength ($\lambda 2$) so as to obtain the attenuation factor of the electromagnetic wave of the first wavelength ($\lambda 1$), and calculate the density of the target substance based upon the attenuation factor in the same manner as in the first embodiment.

In this embodiment, since the sensing resonator 24 is set to resonate the electromagnetic wave having the first wavelength ($\lambda 1$) which is absorbed by the target substance, and the reference resonator 34 is set to resonate the electromagnetic wave having the second wavelength ($\lambda 2$) different from the first wavelength, the electromagnetic wave resonating at the reference resonator 34 can be free from being influenced by the target substance. Thus, the reference resonator 34 is required to be isolated from the atmosphere containing the target substance.

3rd Embodiment

Figure 10:
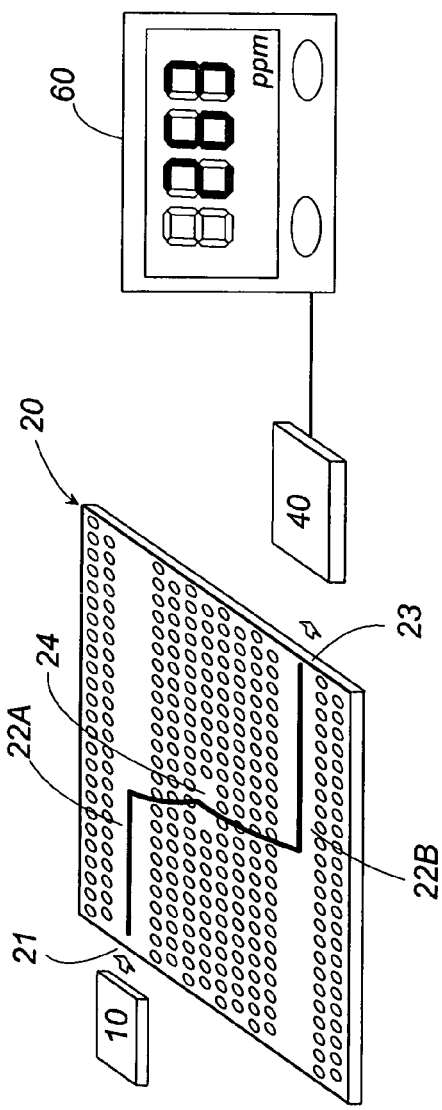
FIG. 10 is a schematic view illustrating a sensor in accordance with a third embodiment of the present invention.
Figure 11:
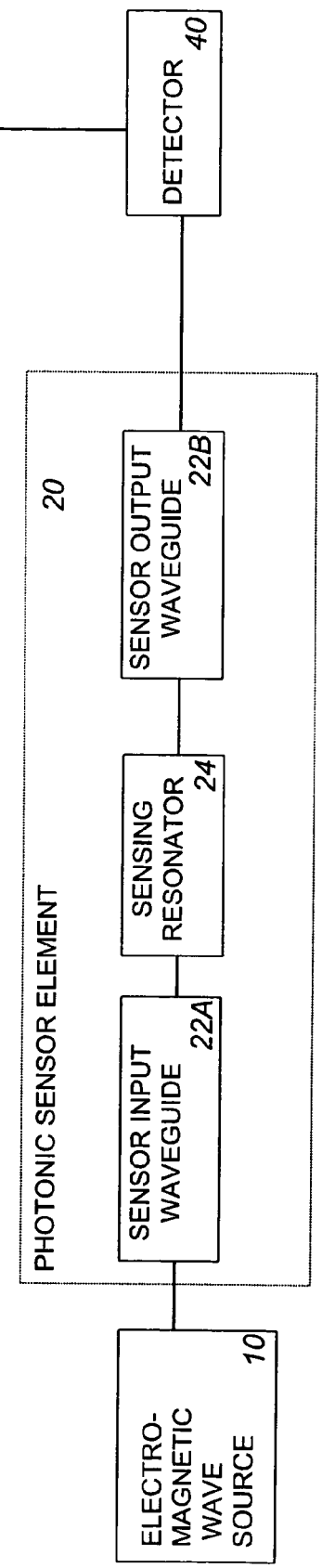
FIG. 11 is a functional block diagram of the above.
Figure 12:
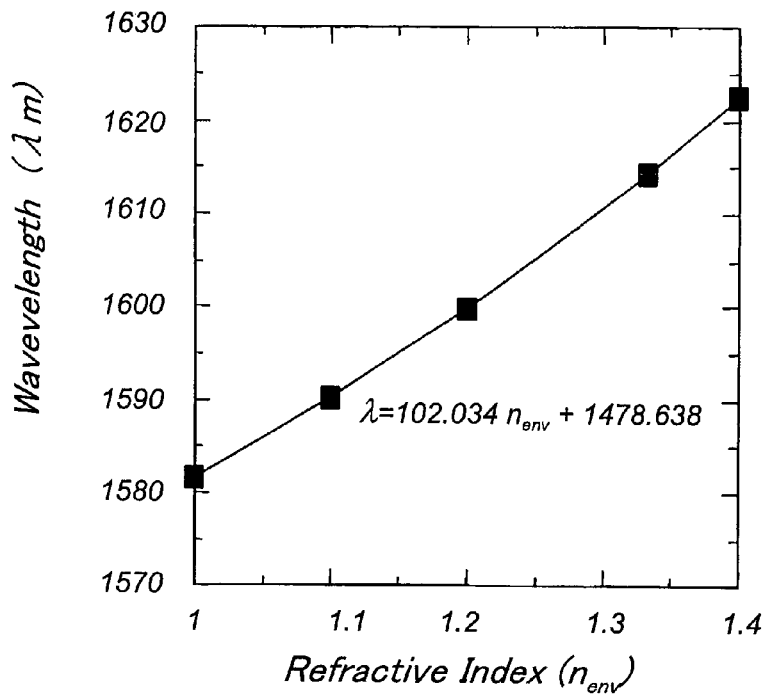
FIG. 12 is a graph illustrating the density detection of the above.

FIGS. 10 and 11 illustrates an embodiment discloses a scheme realized for measurement of the target substance which has a prominent character of altering the refractive index of the atmosphere. The target substance includes, for example, a steam and alcohol. The density measurement of the target substance is made by making the use of the phenomenon that the wavelength that resonates at the sensing resonator will shift in response to the alternation of the refractive index around the sensing resonator caused by the presence of the target substance. FIG. 12 indicates a relation between the refractive index of the target substance and the corresponding wavelength of the electromagnetic wave resonating at the resonator. Thus, by designing the sensing resonator to resonate at the specific wavelength determined by the target substance, the density of the target substance can be regarded as a function of the output intensity emitted from the sensing electrode 24.

For this purpose, the present embodiment is configured to introduce the electromagnetic waves in the wide bandwidth including the specific wavelength to the sensor waveguide 22, to take the intensity of the electromagnetic wave of the specific wavelength inherent to the target substance selectively from the electromagnetic waves emitted from the sensing resonator 24, and calculate the density based upon the electromagnetic intensity. The photonic sensor element 20 of the embodiment illustrated in the figures is configured to have a sensor waveguide compose of an input waveguide 22A and an output waveguide 22B which extend in parallel with each other, and the sensing resonator 24 disposed between the waveguides. The sensing resonator 24 is exposed to the atmosphere containing the target substance such that, when coming into contact with the intended target substance, the resonator resonates the electromagnetic wave of the specific wavelength inherent to the target substance among those introduced through the input port 21 at one lengthwise end of the input waveguide 22A. The resonating electromagnetic wave is then output trough an output port 23 at one lengthwise end of the output waveguide 22B to the detector 40.

The detector 40 is configured to have a spectroscopic analyzing function to select the electromagnetic wave having the specific wavelength determined by the target substance by spectroscopy, obtain the intensity of the selected electromagnetic wave, determine the density of the target substance as proportional to the electromagnetic wave intensity, and output a density signal indicative of the density of the target substance. A display 60 is provided to display the density in response to the density signal.

The electromagnetic wave source 10 supplies the electromagnetic waves in a wide bandwidth including the wavelength determined by the target substance, for example, 2 μm to 13 μm.

FIGS. 13 to 20 illustrate various modifications of the photonic sensor element 20 utilized in the third embodiment as discussed in the above.

Figure 13:
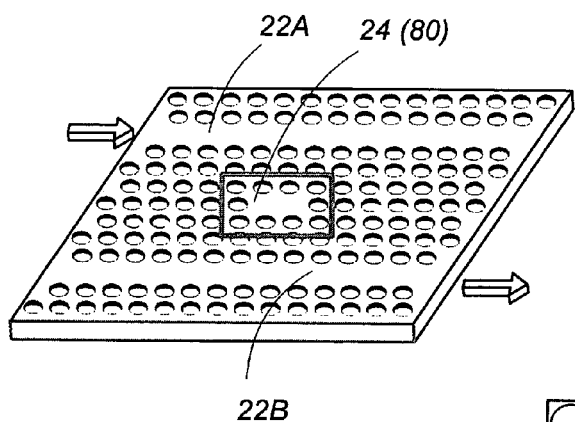
FIG. 13 is a perspective view of a photonic sensor element employed in the above.
Figure 14:
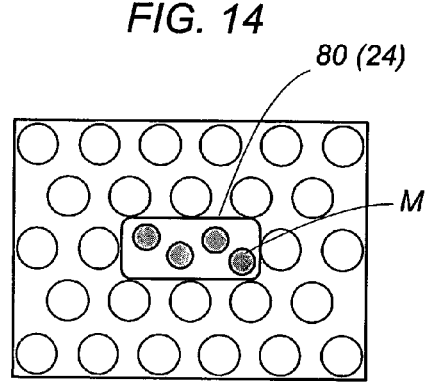
FIG. 14 is an enlarged partial top view of a portion of FIG. 13 including a sensing resonator.
Figure 15:
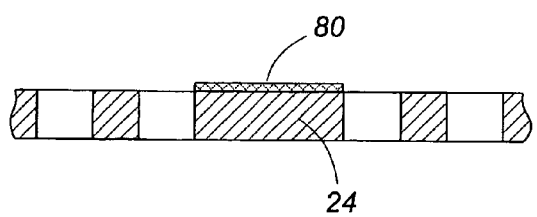
FIG. 15 is an enlarged partial sectional view of the portion of FIG. 13 including a sensing resonator.

In the modification of FIGS. 13 to 15, the sensing resonator 24 is formed on its top with a reactor 80 which absorbs or react with the target substance to alter the wavelength of the electromagnetic wave resonating at the sensing resonator 24. The reactor 80 is provided to positively bring about or exaggerate the wavelength shift in dependence upon the target substance, and is made of a material that significantly alters the refractive index around the resonator 24 due to the presence of the target substance. For example, when realizing a humidity sensor with the target substance of water, SiO2 or polymer of absorbing the water is utilized. When realizing a bio-sensor with the target substance of a biomaterial, a receptor such as carboxylate is utilized. In FIG. 14, "M" is for schematically indicating the molecules of the target substance absorbed to the reactor 80.

Figure 16:
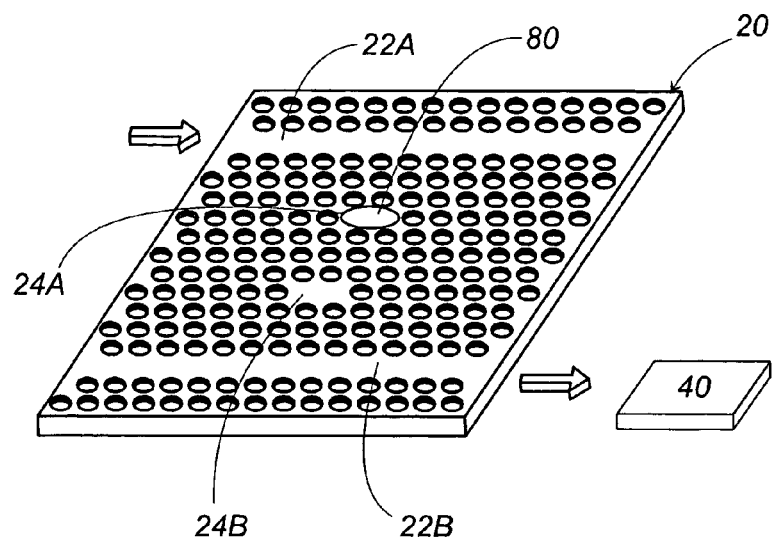
FIG. 16 is a perspective view of another example of the photonic sensor element employed in the above.
Figure 17:
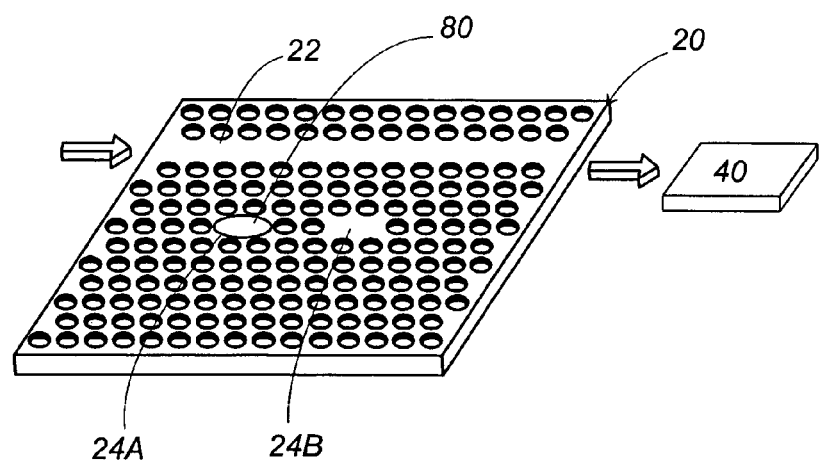
FIG. 17 is a perspective view of a further of the photonic sensor element employed in the above.
Figure 18:
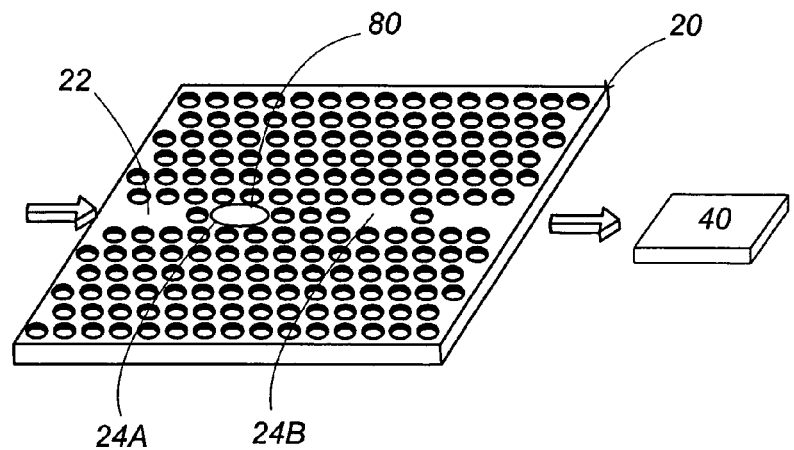
FIG. 18 is a perspective view of a further example of the photonic sensor element employed in the above.

The modification of FIGS. 16 to 18 is configured to have two resonators 24A and 24B within the photonic sensor element 20, and dispose the reactor 80 only on one 24A of the resonators. In the presence of the target substance, the wavelength of the electromagnetic wave resonating at the one resonator 24A is shifted from the wavelength of the electromagnetic wave resonating at the other resonator 24B, thereby weakening an electromagnetic coupling force between the two resonators, and therefore varying the intensity of the electromagnetic wave output to the detector 40. The detector 40 recognizes the variation of the electromagnetic wave intensity to determine the density of the target substance in accordance with the variation. Although the detector 40 is arranged to determine the density based upon the intensity variation of the electromagnetic wave resonating at the resonator provided with the reactor, the intensity of the electromagnetic wave resonating at the reactor without the reactor can be equally relied upon.

In the modification of FIG. 16, two resonators 24A and 24B are arranged between the input waveguide 22A and the output waveguide 22B along a width direction of the photonic sensor element 20. In the modification of FIG. 17, two resonators 24A and 24B are arranged along and outwardly of the waveguide 22. In the modification of FIG. 18, two resonators 24A and 24B are arranged in a row at the center of the waveguide 22.

Figure 19:
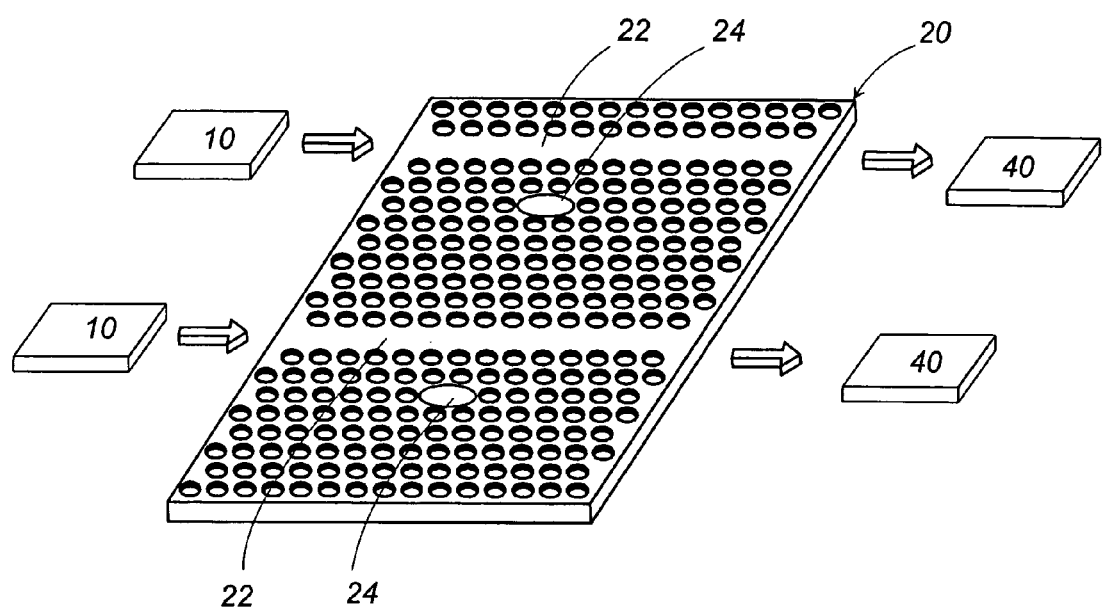
FIG. 19 is a perspective view of a further example of the photonic sensor element employed in the above.

The modification of FIG. 19 is configured to include plural pairs of waveguide 22 and resonator 24 within one photonic sensor element 20, and include a set of an electromagnetic wave source 10 and a detector 40 for each pair. The resonators 24 are designed to resonate the electromagnetic wave having wavelengths different from each other for density measurement of the plural kinds of the target substances. In this case, at least one of the resonators may be provided with the above-mentioned reactor.

Figure 20:
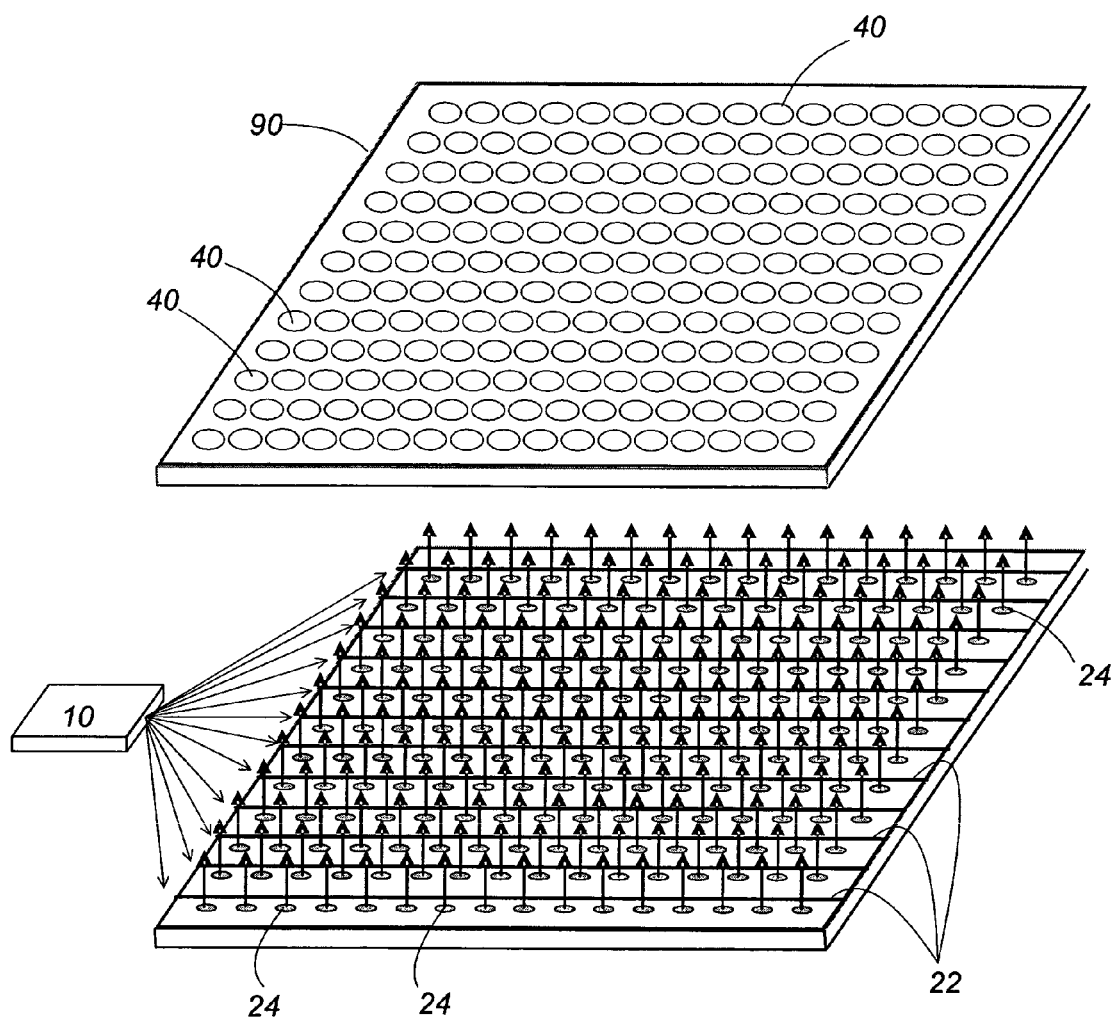
FIG. 20 is a perspective view of a still further example of the photonic sensor element employed in the above.

The modification of FIG. 20 is configured as a planar sensor in which a plurality of parallel waveguides 22 are provided within a single photonic sensor element 20 along one dimension thereof, and a plurality of resonators 24 are arranged crosswise within a two-dimensional plane. The electromagnetic wave from a single electromagnetic wave source 10 is introduced to each of the waveguides 22, while the resonators 24 are coupled respectively to detectors 40. The detectors 40 are arranged also in a two-dimensional plane and supported by a frame 90. Each detector 40 is spaced from the plane of the resonators 24 in a direction perpendicular thereto to receive the electromagnetic wave emitted from each of the resonators 24. The resonators 24 are designed to be electromagnetically coupled to the adjacent waveguides 22 and to resonate the electromagnetic waves having the wavelengths different from each other, thereby enabling to recognize an in-plane refractive index variation, i.e., the target substance varying in a plane. That is, the electromagnetic wave intensities from different resonators 24 denote the density of the different target substances, respectively. Therefore, it is possible to detect a reaction progress that the target substance undergoes, for example, and also possible to detect an in-plane distribution of the target substances, other than the density detection. When the plural resonators 24 are designed to resonate the electromagnetic wave of the same wavelength, it is possible to obtain an in-plane density distribution of a particular target substance. Also in this modification, the resonator may be additionally provided with the reactor.

4th Embodiment

Figure 21:
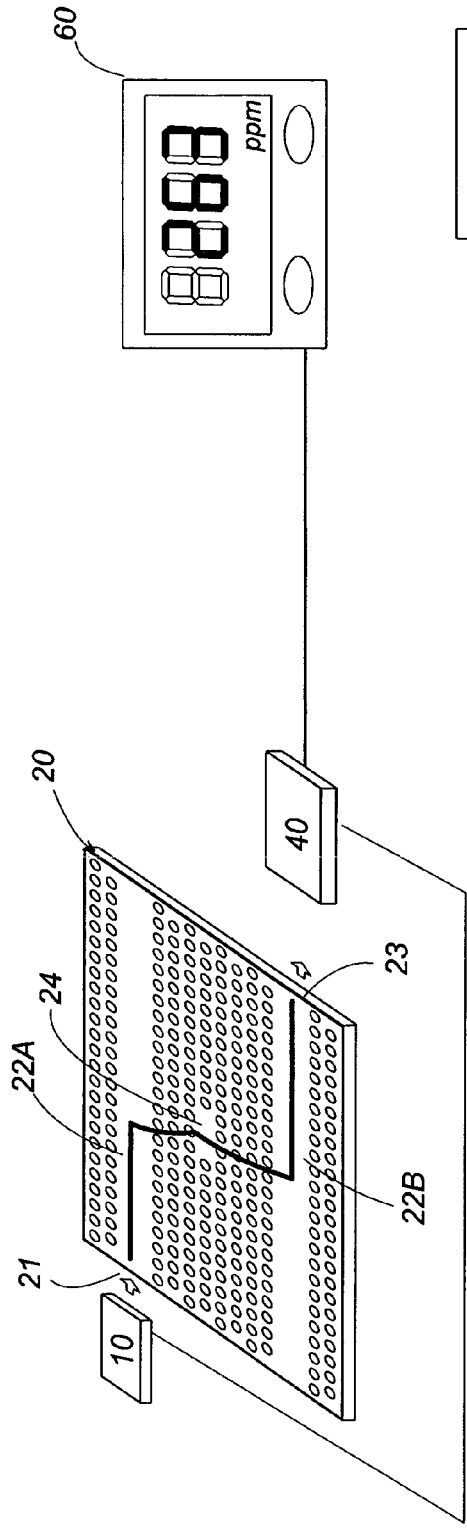
FIG. 21 is a schematic view illustrating a sensor in accordance with a fourth embodiment of the present invention.
Figure 22:
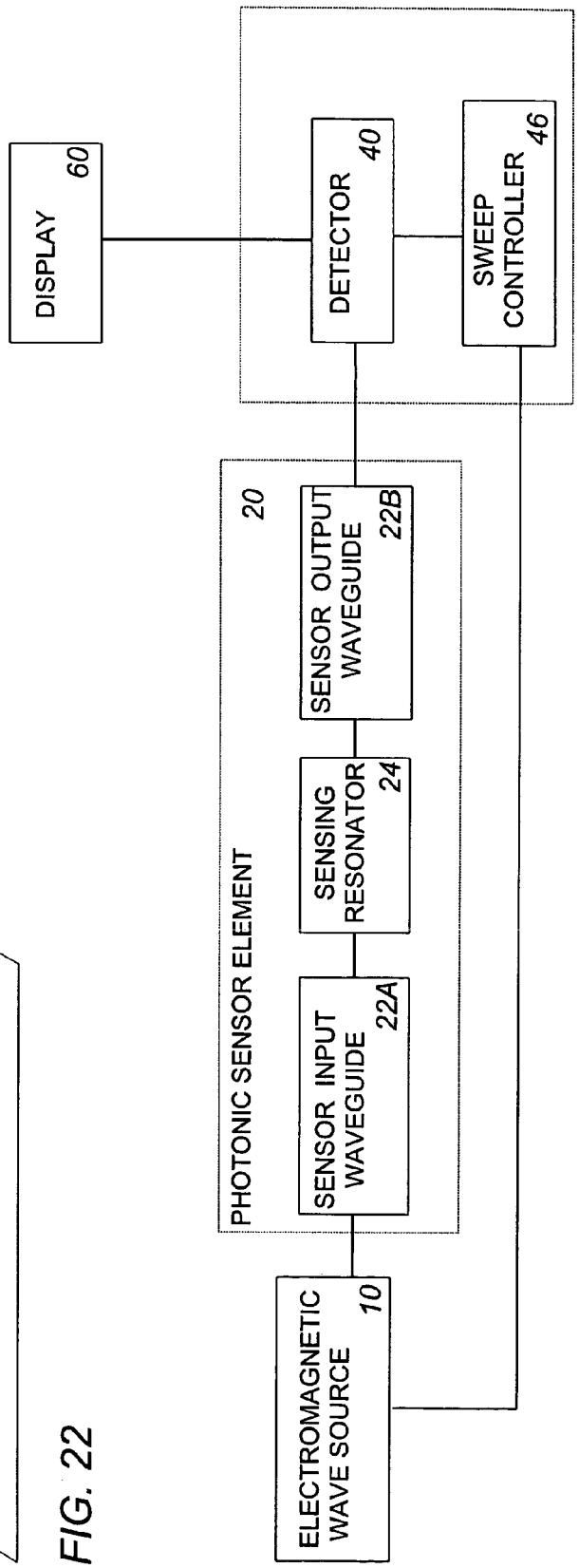
FIG. 22 is a functional block diagram of the above.

FIGS. 21 and 22 illustrates a fourth embodiment of the present invention which is basically identical to the third embodiment, but employs an electromagnetic wave source 10 supplying electromagnetic waves of variable wavelengths such that the photonic sensor element 20 is given the electromagnetic wave of which wavelength varies with time by wavelength sweep. The range of the wavelength sweep is set to include the specific wavelength determined by a refractive index of a target substance. The density measurement is made by a detector 40 which obtains the magnetic wave intensity from a resonator 24 at a time when the electromagnetic wave of the specific wavelength is introduced from the electromagnetic wave source 10. For this purpose, the present embodiment includes a sweep controller 46 which varies the wavelength of the electromagnetic wave from the source 10 with time, and at the same time synchronizes the readout of the electromagnetic wave output with the wavelength sweep. For density measurement, the intensity of the electromagnetic wave having the wavelength different from the specific wavelength corresponding to the target substance is stored as a reference intensity with which the intensity of the electromagnetic wave of the specific wavelength is compared for calculation of the density of the target substance. With this arrangement, it is possible to analyze the electromagnetic wave intensity for each of the wavelengths varying within the range of the wavelength sweep, and therefore to obtain the densities of the target substances of various kinds. In addition to the structure of FIG. 21, the photonic sensor element 20 of the present embodiment may have anyone of the structures as shown in FIGS. 5 to 8, and FIGS. 13 to 18.

Further, the present embodiment can incorporate a configuration of cyclically modulating the intensity of the electromagnetic wave emitted from the resonator or the intensity of the electromagnetic wave supplied from the electromagnetic wave source to the resonator for enhancing the measurement accuracy.

5th Embodiment

Figure 23:
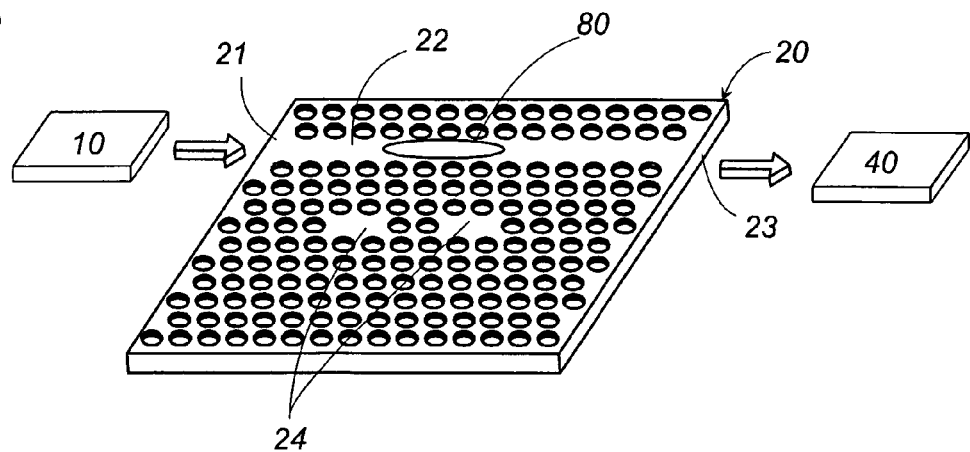
FIG. 23 is a schematic view illustrating a sensor in accordance with a fifth embodiment of the present invention.

FIG. 23 illustrates a fifth embodiment of the present invention in which the above-explained reactor 80 is disposed in an electromagnetic wave path extending through the resonator 24 within the photonic sensor element 20. When the reactor 80 absorbs or reacts with the target substance, electromagnetic coupling efficiency in the electromagnetic wave path (energy coupling path), i.e., an effective waveguide length varies to correspondingly vary the electromagnetic wave intensity detected at the detector 40. It is the electromagnetic wave intensity variation that is relied upon for density measurement of the target substance. In this embodiment, the reactor 80 is disposed in the center of the waveguide 22 formed at its opposite ends respectively with the input port 21 and the output port 23, in order to vary the electromagnetic coupling efficiency with the resonator 24 disposed adjacent to the center of the waveguide 22 in the presence of the target substance.

Figure 24:
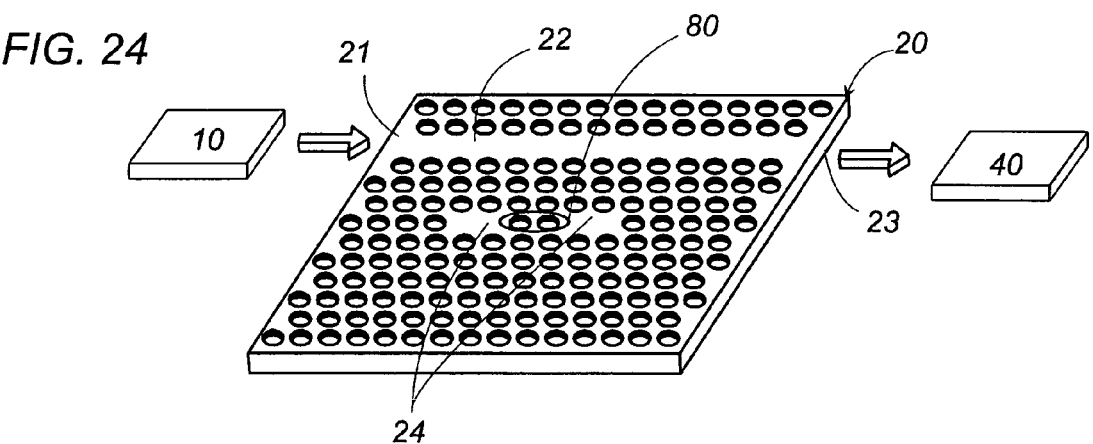
FIG. 24 is a perspective view of another example of the photonic sensor element employed in the above.

FIG. 24 illustrates a modification of the fifth embodiment in which the reactor 80 is formed between the two resonators 24 arranged in parallel with the waveguide 22 within the photonic sensor element 20 for density measurement of the target substance based upon the variation of the electromagnetic coupling efficiency between the two resonators.

Figure 25:
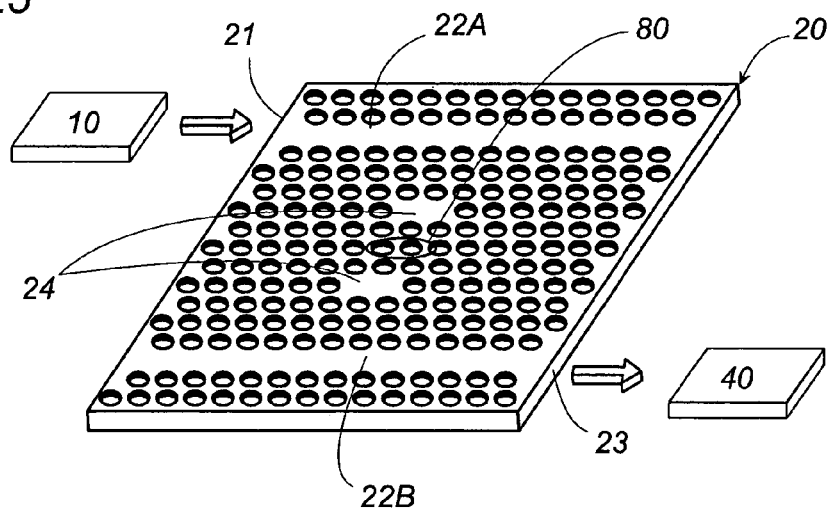
FIG. 25 is a perspective view of a further of the photonic sensor element employed in the above.

FIG. 25 illustrates a modification of the fifth embodiment in which the reactor 80 is formed between the two resonators 24 arranged between the two parallel ones of the input waveguide 22A and the output waveguide 22B within the photonic sensor element 20 for density measurement of the target substance based upon the variation of the electromagnetic coupling efficiency between the two resonators.

6th Embodiment

Figure 26:
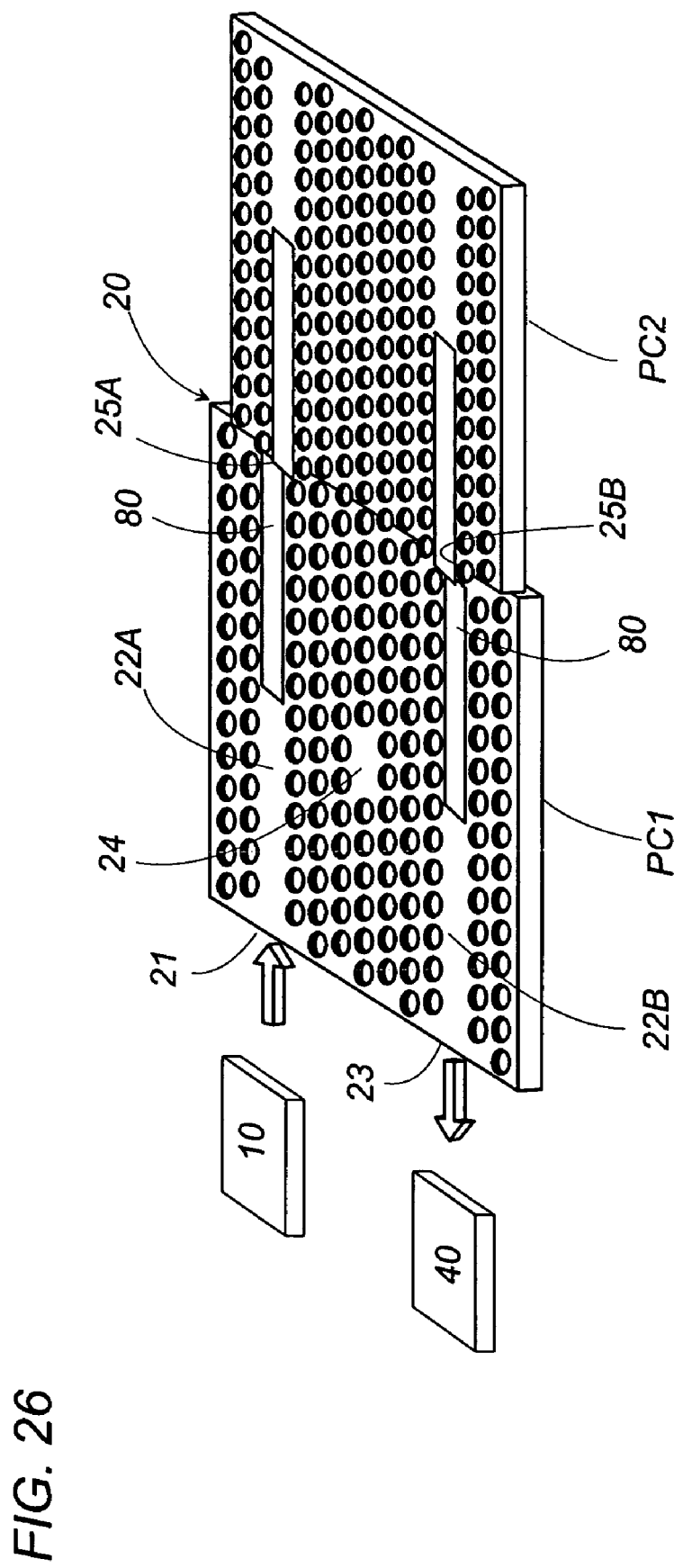
FIG. 26 is a schematic view illustrating a sensor in accordance with a sixth embodiment of the present invention.

FIG. 26 illustrates a fifth embodiment of the present invention in which the photonic sensor element 20 is configured to have a first photonic crystalline structure PC1 and a second photonic crystalline structure PC2 which has a different crystalline structure from the first crystalline structure but is formed continuously therefrom. In these crystalline structures, minute circular pores for varying the refractive index are arranged in a two-dimensional array at different cycles from each other in order to selectively propagate the electromagnetic waves of different wavelengths. An input waveguide 22A and an output waveguide 22B are each formed to bridge over the first crystalline structure PC1 and the second crystalline structure PC2. At one end of the first crystalline structure PC1, the input waveguide 22A and the output waveguide 22B are formed respectively with an input port 21 and an output port 23 of the electromagnetic wave. A resonator 24 is disposed between the input waveguide 22A and the output waveguide 22B within the first photonic crystalline structure PC1 to be electromagnetically coupled to both of the waveguides. The resonator 24 is designed to resonate the electromagnetic wave of the specific wavelength.

The input waveguide 22A is formed at an interface between the first crystalline structure PC1 and the second crystalline structure PC2 with an input reflector 25A which reflects only the electromagnetic wave of the specific wavelength resonating at the resonator and passes the electromagnetic waves of the other wavelengths. Likewise, the output waveguide 22B is formed at the interface between the first crystalline structure PC1 and the second crystalline structure PC2 with an output reflector 25A which reflects only the electromagnetic wave of the specific wavelength resonating at the resonator and passes the electromagnetic waves of the other wavelengths. The reflectors are formed by the fact that the first crystalline structure PC1 and the second crystalline structure PC2 have the cyclic structure different from each other, and are responsible for improving efficiency of propagating the electromagnetic wave of the specific wavelength allowed to resonate at the resonator 24 from the input waveguide 22A to the resonator 24, and efficiency of outputting the electromagnetic wave of the specific wavelength resonating at the resonator 24 to the detector 40 through the output waveguide 22B.

The input waveguide 22A and the output waveguide 22B are formed respectively at portions bridging the first crystalline structure PC1 and the second crystalline structure PC2 with the above-explained reactors 80 which, upon reacting with the target substance, alters the character of the interface between the crystalline structures to vary the functions at the input reflector 25A and the output reflector 25B, thereby significantly lowering the function of reflecting the electromagnetic wave of the specific wavelength resonating at the resonator 24. Thus, upon recognition of the target substance at the reactor 80, the intensity of the electromagnetic wave of the specific wavelength emitted from the output waveguide 22B is lowered such that the density of the target substance can be calculated based upon the variation of the electromagnetic wave intensity. That is, a drop efficiency (D) is obtained from the electromagnetic wave intensity received at the detector 40, and the density is obtained from the drop efficiency. The drop efficiency (D) is a ratio of the output electromagnetic wave intensity $S_{-2}$ to the input electromagnetic wave intensity $S_{+1}$, as expressed by the above equation 3.

The drop efficiency (D) is also expressed by the following equation.

$$D = \left|\frac{S_{-2}}{S_{+1}}\right|^2 = \frac{\{Q_{inb}/(1+\cos\theta_1) \cdot Q_{inr}/(1+\cos\theta_2)\}}{4\left(\frac{\omega-\omega_0'}{\omega_0}\right)^2 + \left\{\frac{1}{Q_V} + \frac{1}{Q_{inb}/((1+\cos\theta_1))} + \frac{1}{Q_{inr}/((1+\cos\theta_2))}\right\}^2} \quad \text{(equation 4)}$$

$$\theta_1 = 2\beta_1 \times d_1 + \Delta_1 \quad \text{(equation 5)}$$

$$\theta_2 = 2\beta_2 \times d_2 + \Delta_2 \quad \text{(equation 6)}$$

$$Q_{inb} = \omega_0 \times W \bigg/ \left(-\frac{dW}{dt}\right) \quad \text{(equation 7)}$$

$$Q_{inb} = \omega_0 \times W \bigg/ \left(-\frac{dW}{dt}\right) \quad \text{(equation 8)}$$

$$\omega_0' = \omega_0\left(1 + \frac{\sin\theta_1}{2Q_{inb}} + \frac{\sin\theta_2}{2Q_{inr}}\right) \quad \text{(equation 9)}$$

In the above equation, $d_1$ is a distance between resonator 24 and input reflector 25A along a length of input waveguide 22A;
$d_2$ is a distance between resonator 24 and output reflector 25B along a length of output waveguide 22B;
$\beta_1$ is a propagation factor of input waveguide 22A;
$\beta_2$ is a propagation factor of output waveguide 22B;
$\Delta_1$ is a reflecting phase variation of electromagnetic wave reflected on input reflector 25A;
$\Delta_2$ is a reflecting phase variation of electromagnetic wave reflected on output reflector 25B;
$\theta_1$ is a phase shift amount of electromagnetic wave reflected on input reflector 25A and proceeding back to around resonator 24;
$\theta_2$ is a phase shift amount of electromagnetic wave reflected on output reflector 25B and proceeding back to around resonator 24;
$\omega_0$ is a resonant frequency at resonator 24;
$Q_{inb}$ is a Q-value between resonator 24 and input waveguide 22A;
$Q_{inr}$ is a G-value between resonator 24 and output waveguide 22B;
W is an energy accumulated in resonator 24; and
dW/dt is an energy lost per unit time from resonator 24 to input waveguide 22A, an energy lost per unit time from resonator 24 to output waveguide 22B.

Since the photonic sensor element 20 of the present embodiment is configured to realize the photonic crystalline structure by forming a large number of minute circular pores in the silicon semiconductor layer superimposed on $SiO_2$ substrate, in which the resonator 24 is made as a donor-type defect formed by elimination of the circular pores, i.e., by filling the pores with silicon, radiation loss to free space is small to give a high $Q_v$ so that $Q_{inb}/(1+\cos\theta_1) \ll Q_v$. Thus, the term "$1/Q_v$" in the above equation 4 can be ignored. Thus, it is enabled to give the drop efficiency of about 1 (i.e., 100%) in the absence of the target substance by setting the parameters $d_1$, $d_2$, $\beta_1$, $\beta_2$, $\Delta_1$, $\Delta_2$, $\theta_1$, $\theta_2$, $Q_{inb}$, $Q_{inr}$, $Q_v$ which satisfy the relations $Q_{inb}/(1+\cos\theta_1) = Q_{inr}/(1+\cos\theta_2)$ and $\theta_1$, $\theta_2 \neq 2N\pi$ (N=0, 1, ...), which differs the drop efficiency to a greater extent in the presence of the target substance and enables a highly sensitive density measurement.

It is noted in this connection that although the above embodiments employs the photonic crystal of silicon semiconductor as the photonic sensor element, the present invention should not be limited thereto, and may employs various photonic crystals such as GaAs and InP.

Further, the wavelength of the electromagnetic wave supplied from the electromagnetic wave source to the photonic sensor element can be suitable selected in accordance with the kind of the target substance. The applicable electromagnetic wave may be suitable selected from those of optical transmission bandwidth such as C-band (1530 nm to 1565 nm) and L-band (1565 nm to 1625 nm) based upon the target substance. Further, the electromagnetic wave source 10 may be selected from those generating the electromagnetic waves of the optical transmission bandwidth including light emitting diode, semiconductor laser, halogen lamp, ASE (Amplified Spontaneous Emission) light source, and SC (supercontinuum) light source. When generating the near infrared wavelength band, it is possible to employ a black body emission light source such as an infrared radiation element of so-called micro-bridge structure in which linear heaters bridge between two points on one face of a rectangular supporting substrate fabricated by a micro-machining technology with the use of a silicon substrate, for example.

Although the above embodiments disclose the structures for detection of the density of the predetermined target substance, the present invention should not be limited thereto and can be equally applied for detection of the kind or characteristic of the target substance through analysis of the electromagnetic wave intensity output from the photonic sensor element.

Further, although the above embodiments disclose the use as the gas sensor, humidity sensor and bio-sensor, the present invention should not be limited thereto and can be utilized as sensors for detection of other substances such as an ion sensor.

The subject application claims a priority of Japanese application no. 2004-87666 filed on Mar. 24, 2004 and incorporates all the contents disclosed in the Japanese application.

The invention claimed is:

1. A sensor for determining a characteristic of a target substance, said sensor comprising:
    an electromagnetic wave source of supplying an electromagnetic wave;
    a photonic sensor element having a photonic crystalline structure and configured to include:
        a sensor waveguide for introducing said electromagnetic wave, and
        a sensing resonator electromagnetically coupled to said sensor waveguide for resonating the electromagnetic wave of a specific wavelength, said sensing resonator being exposed to an atmosphere including the target substance so as to vary a characteristic of said electromagnetic wave emitted from said sensing resonator; and
    a detector configured to receive the electromagnetic wave emitted from said sensing resonator to recognize an intensity variation of the electromagnetic wave and issue a signal indicative of a characteristic of said target substance;
    wherein said detector is configured to determine a density of said target substance based upon a characteristic variation of said electromagnetic wave and issue said signal indicative of the density of the target substance, wherein said photonic sensor element includes within said photonic crystalline structure a reference waveguide; and a reference resonator, said reference waveguide introducing said electromagnetic wave from said source, said reference resonator being electromagnetically coupled to said reference waveguide to resonate the introduced electromagnetic waver at said specific wavelength, said reference resonator being concealed from said target substance, said detector comprising:
- an output intensity meter providing a detection signal indicating an intensity of the electromagnetic wave of said specific wavelength emitted from said sensing resonator;
- a reference intensity meter providing a reference signal indicating an intensity of the electromagnetic wave of said specific wavelength emitted from said reference resonator; and
- a density meter comparing said detection signal with said reference signal so as to obtain an attenuation of the electromagnetic wave of said specific wavelength, thereby calculating the density of said target substance based upon said attenuation.

2. The sensor as set forth in claim 1, wherein said photonic sensor element has the photonic crystalline structure arranged in a two-dimensional array;

each of said sensor waveguide and said reference waveguide extending within the two dimensional photonic crystalline structure to define an input port and an output port respectively on opposite ends of said waveguide, each of said input ports being disposed to receive said electromagnetic wave from said source, each of said output ports being coupled to each corresponding one of said output intensity meter and said reference intensity meter for providing the electromagnetic wave emitted from each corresponding one of said sensing resonator and said reference resonator.

3. The sensor as set forth in claim 1, wherein said photonic sensor element has the photonic crystalline structure arranged in a two-dimensional array;

each of said sensor waveguide and said reference waveguide extending within the two dimensional photonic crystalline structure to define an input port and an output port respectively on opposite ends of said waveguide, said sensing resonator and said reference resonator being disposed respectively within said sensor waveguide and said reference waveguide, each of said input ports being disposed to receive said electromagnetic wave from said source, each of said output ports being coupled to each corresponding one of said output intensity meter and said reference intensity meter for providing the electromagnetic wave emitted from each corresponding one of said sensing resonator and said reference resonator.

4. The sensor as set forth in claim 3, wherein a plurality of said sensing resonators are aligned along said sensor waveguide.

5. The sensor as set forth in claim 1, wherein said photonic sensor element has the photonic crystalline structure arranged in a two-dimensional array;

each of said sensor waveguide and said reference waveguide extends within the two dimensional photonic crystalline structure to define an input port at one lengthwise end thereof, each of said input ports being disposed to receive said electromagnetic wave from said source, said photonic sensor element further including a sensing output waveguide and a reference output waveguide, said sensing output waveguide and said reference output waveguide extending in parallel with corresponding ones of said sensor waveguide and said reference waveguide, and being electromagnetically coupled respectively to said sensor resonator and said reference resonator, each of said sensing output waveguide and said reference output waveguide defining at its one lengthwise end an output port which is coupled to each corresponding one of said output intensity meter and said reference intensity meter.

6. The sensor as set forth in claim 1, wherein said photonic sensor element has the photonic crystalline structure arranged in a two-dimensional array;

each of said sensor waveguide and said reference waveguide extends within said two dimensional photonic crystalline structure to define an input port on one lengthwise end thereof;

each of said input ports being disposed to receive said electromagnetic wave from said source, each of said output intensity meter and said reference intensity meter being disposed in a spaced relation from a plane of said photonic sensor element and being coupled to each corresponding one of said sensing resonator and said reference resonator to receive the electromagnetic wave emitted therefrom.

7. The sensor as set forth in claim 1, wherein said electromagnetic wave source supplies the electromagnetic wave including different wavelengths so that said sensing resonator allows the resonance of the electromagnetic wave of said specific wavelength which is determined by said target substance, said detector being configured to select the electromagnetic wave of said specific wavelength emitted from said sensing resonator and calculate the density of the target substance based upon the intensity of thus selected electromagnetic wave.

8. The sensor as set forth in claim 7, wherein said sensing waveguide is cooperative with said sensing resonator and said detector to define a single detection unit for detection of said target substance of a particular kind, said sensor including a plurality of said detection units in which said sensing resonators are configured to resonate the electromagnetic wave of the wavelengths which are different from each other for sensing the target substances of different kinds.

9. The sensor as set forth in claim 7, wherein said sensing resonator is provided with a reactor that reacts with said target substance to modify the wavelength of the electromagnetic wave resonating in said sensing resonator for resonating the electromagnetic wave at said specific wavelength.

10. The sensor as set forth in claim 7, wherein said photonic sensor element includes two said sensing resonators, one of said sensing resonators being provided with a reactor which reacts with said target substance to vary the wavelength of the electromagnetic wave resonating in said sensing resonator, said two sensing resonators being electromagnetically coupled to give a composite magnetic wave issued to said detector.

11. The sensor as set forth in claim 7, wherein
a plurality of said sensing resonators are arranged in the two-dimensional array,
a plurality of said detectors are arranged in a two-dimensional array and coupled respectively to said sensing resonators to obtain the intensity of the electromagnetic wave of said specific wavelength,
said detectors being configured to calculate the density with regard to each of said sensing resonators, giving a density distribution across the array of said sensing resonators.

12. The sensor as set forth in claim 1, wherein
said electromagnetic wave source supplies the electromagnetic wave of different wavelengths so that said sensing resonator is allowed to resonate the electromagnetic wave of said specific wavelength,
a plurality of said detectors are arranged in a two-dimensional array and coupled respectively to said sensing resonators to obtain the intensity of the electromagnetic wave of said specific wavelength,
said plural sensing resonators being configured to resonate the electromagnetic wave of different wavelengths,
said plural detectors being configured to detect the presence of the target substances of different kinds based upon the intensity of the electromagnetic waves emitted respectively from said sensing resonators, thereby giving a two-dimensional distribution of the target substances of different kinds.

13. The sensor as set forth in claim 1, wherein
said sensing resonator is configured to resonate said electromagnetic wave of said specific wavelength,
a reactor is provided in said sensor waveguide at a portion electromagnetically coupled to said sensing resonator,
said reactor being configured to react with said target substance to alter an effective waveguide length between said sensor waveguide to said sensing resonator to thereby vary the intensity of the electromagnetic wave received at said target detector,
said detector being configured to calculate the density of the target substance based upon the variation of the intensity of the electromagnetic wave.

14. The sensor as set forth in claim 1, wherein
two said sensing resonators are formed in said photonic sensor element and are electromagnetically coupled to each other, said sensing resonators being configured to resonate said electromagnetic wave of said specific wavelength,
a reactor is provided in an energy coupling path between said two sensing resistors, said reactor being configured to react with said target substance to alter an effective waveguide length of said energy coupling path to thereby vary the intensity of the electromagnetic wave emitted from said sensing resonators,
said detector being configured to calculate the density of the target substance based upon the variation of the intensity of the electromagnetic wave.

15. The sensor as set forth in claim 1, further including:
a controller configured to monitor an environmental parameter indicative of an environmental condition,
said controller modifying an optical characteristic of said sensing resonator based upon the environmental parameter to resonate the electromagnetic wave at said specific wavelength.

16. The sensor as set forth in claim 15, wherein
said photonic sensor element is provided with a heater which is actuated by said controller to modify said optical characteristic of said sensing resonator.

17. The sensor as set forth in claim 1, further including:
a refresh means configured to eliminate the target substance or impurities trapped on said sensing resonator.

18. The sensor as set forth in claim 17, wherein
said refresh means is a heater provided on the side of said photonic sensor element to dissipate the target substance or impurities from the surface of said sensing resonator by heat.

19. The sensor as set forth in claim 1, further including:
modulating means configured to modulate one of wavelength and intensity of said electromagnetic wave supplied from said source to said waveguide.

20. A sensor for determining a characteristic of a target substance, said sensor comprising:
an electromagnetic wave source of supplying an electromagnetic wave;
a photonic sensor element having a photonic crystalline structure and configured to include:
a sensor waveguide for introducing said electromagnetic wave, and
a sensing resonator electromagnetically coupled to said sensor waveguide for resonating the electromagnetic wave of a specific wavelength, said sensing resonator being exposed to an atmosphere including the target substance so as to vary a characteristic of said electromagnetic wave emitted from said sensing resonator; and
a detector configured to receive the electromagnetic wave emitted from said sensing resonator to recognize an intensity variation of the electromagnetic wave and issue a signal indicative of a characteristic of said target substance,
wherein said detector is configured to determine a density of said target substance based upon a characteristic variation of said electromagnetic wave and issue said signal indicative of the density of the target substance,
wherein said photonic sensor element includes a first photonic crystalline structure and a second photonic crystalline structure which are of different configuration and arranged in side-by-side relation within a two-dimension,
said sensor waveguide comprising:
an input waveguide extending across said first and second photonic crystalline structures;
a first output waveguide extending within a confine of said first crystalline structure;
a second output waveguide extending within a confine of said second crystalline structure,
said sensing resonator being formed within said first crystalline structure;
said second crystalline structure including a reference resonator which causes a resonance of the electromagnetic wave of a wavelength different from said specific wavelength inherent to said sensing resonator;
said detector comprising:
an output intensity meter configured to provide a detection signal indicative of the intensity of the electromagnetic wave of said specific wavelength emitted from said sensing resonator;
a reference intensity meter configured to provide a referenced signal indicative of the intensity of the electromagnetic wave emitted from said reference resonator; and a density meter configured to compare said detection signal with said reference signal so as to obtain an attenuation of the electromagnetic wave of said specific wavelength at said sensing resonator, thereby calculating a density of said target substance as a function of said attenuation.

21. A sensor for determining a characteristic of a target substance, said sensor comprising:
an electromagnetic wave source of supplying an electromagnetic wave;
a photonic sensor element having a photonic crystalline structure and configured to include:
a sensor waveguide for introducing said electromagnetic wave, and
a sensing resonator electromagnetically coupled to said sensor waveguide for resonating the electromagnetic wave of a specific wavelength, said sensing resonator being exposed to an atmosphere including the target substance so as to vary a characteristic of said electromagnetic wave emitted from said sensing resonator; and
a detector configured to receive the electromagnetic wave emitted from said sensing resonator to recognize an intensity variation of the electromagnetic wave and issue a signal indicative of a characteristic of said target substance,
wherein, said detector is configured to determine a density of said target substance based upon a characteristic variation of said electromagnetic wave and issue said signal indicative of the density of the target substance,
wherein said electromagnetic wave source is configured to sweep the electromagnetic wave for varying the wavelength thereof with respect to time so that said sensing resonator allows the resonance of the electromagnetic wave of a specific wavelength which is determined by said target substance,
said detector is configured to give an intensity of the electromagnetic wave at said specific wavelength emitted from said sensing resonator and calculate the density of the target substance based upon said intensity of the electromagnetic wave.

22. The sensor as set forth in claim 21, wherein
said sensing waveguide is cooperative with said sensing resonator and said detector to define a single detection unit for detection of said target substance of a particular kind,
said sensor including a plurality of said detection units in which said sensing resonators are configured to resonate the electromagnetic wave of the wavelengths which are different from each other for sensing the target substances of different kinds.

23. The sensor as set forth in claim 21, wherein
said sensing resonator is provided with a reactor that reacts with said target substance to modify the wavelength of the electromagnetic wave resonating in said sensing resonator for resonating the electromagnetic wave at said specific wavelength.

24. The sensor as set forth in claim 21, wherein
said photonic sensor element includes two said sensing resonators,
one of said sensing resonators being provided with a reactor which reacts with said target substance to vary the wavelength of the electromagnetic wave resonating in said sensing resonator,
said two sensing resonators being electromagnetically coupled to give a composite magnetic wave issued to said detector.

25. The sensor as set forth in claim 21, wherein
a plurality of said sensing resonators are arranged in the two-dimensional array,
a plurality of said detectors are arranged in a two-dimensional array and coupled respectively to said sensing resonators to obtain the intensity of the electromagnetic wave of said specific wavelength,
said detectors being configured to calculate the density with regard to each of said sensing resonators, giving a density distribution across the array of said sensing resonators.

26. The sensor as set forth in claim 21 further comprising a sweep controller, wherein said sweep controller is configured to vary the wavelength of the electromagnetic wave from said electromagnetic wave source, and at the same time synchronizes readout of an output of the electromagnetic wave from the electromagnetic wave source with wavelength sweep.

27. A sensor for determining a characteristic of a target substance, said sensor comprising:
an electromagnetic wave source of supplying an electromagnetic wave;
a photonic sensor element having a photonic crystalline structure and configured to include:
a sensor waveguide for introducing said electromagnetic wave, and
a sensing resonator electromagnetically coupled to said sensor waveguide for resonating the electromagnetic wave of a specific wavelength, said sensing resonator being exposed to an atmosphere including the target substance so as to vary a characteristic of said electromagnetic wave emitted from said sensing resonator; and
a detector configured to receive the electromagnetic wave emitted from said sensing resonator to recognize an intensity variation of the electromagnetic wave and issue a signal indicative of a characteristic of said target substance,
wherein said photonic sensor element includes a first photonic crystalline structure and a second photonic crystalline structure which are different from each other and are arranged in a side-by-side relation within a two-dimensional array,
said sensor waveguide is composed of an input waveguide and an output waveguide which extend in parallel with each other, each of said input and output waveguides extending over the full length of said first photonic crystalline structure into said second photonic crystalline structure,
said sensing resonator being formed in said first crystalline structure between said input waveguide and said output waveguide,
said input waveguide defining at its one lengthwise end away from said second crystalline structure an input port for receiving said electromagnetic wave from said source,
said output guide defining at its one lengthwise end away from said second crystalline structure an output port for emitting the electromagnetic wave of said specific wavelength resonating at said sensing resonator,
said input waveguide being formed with an input reflector at the interface between the first and second crystalline structures for reflecting the electromagnetic wave of said specific wavelength towards said output port, said output waveguide being formed with an output reflector at the interface between the first and second crystalline structures for reflecting the electromagnetic wave of said specific wavelength towards said input port, each of said input waveguide and said output waveguide being provided with a reactor at a portion bridging across said first and second crystalline structures, said reactor being configured to react with said target substance to alter reflection efficiency at said input reflector and said output reflector, thereby varying the intensity of the electromagnetic wave received at said target detector, and said detector being configured to calculate the density of the target substance based upon the variation of the intensity of the electromagnetic wave.

* * * * *